United States Patent
Flitsch et al.

(10) Patent No.: US 11,048,230 B2
(45) Date of Patent: Jun. 29, 2021

(54) METHOD AND APPARATUS FOR A TISSUE ENGINEERING SYSTEM

(71) Applicant: Organofab Technologies, Inc., New Windsor, NY (US)

(72) Inventors: Frederick A. Flitsch, New Windsor, NY (US); Robert A. Flitsch, New Windsor, NY (US); Brent Chanin, Goshen, NY (US); Rudiger Hilken, Beacon, NY (US)

(73) Assignee: Organofab Technologies, Inc., New Windsor, NY (US)

( * ) Notice: Subject to any disclaimer, the term of this patent is extended or adjusted under 35 U.S.C. 154(b) by 80 days.

(21) Appl. No.: 16/331,661

(22) PCT Filed: Jun. 5, 2018

(86) PCT No.: PCT/US2018/035984
§ 371 (c)(1),
(2) Date: Mar. 8, 2019

(87) PCT Pub. No.: WO2018/226642
PCT Pub. Date: Dec. 13, 2018

(65) Prior Publication Data
US 2019/0346829 A1    Nov. 14, 2019

Related U.S. Application Data

(60) Provisional application No. 62/515,983, filed on Jun. 6, 2017.

(51) Int. Cl.
| | | |
|---|---|---|
| *G05B 19/4099* | (2006.01) |
| *B33Y 10/00* | (2015.01) |
| *B33Y 30/00* | (2015.01) |
| *B33Y 50/02* | (2015.01) |
| *B33Y 70/00* | (2020.01) |
| *A61L 27/38* | (2006.01) |
| *B01L 3/00* | (2006.01) |
| *C12M 3/00* | (2006.01) |
| *C12M 3/06* | (2006.01) |
| *C12N 5/00* | (2006.01) |
| *C12N 5/071* | (2010.01) |
| *C12N 5/074* | (2010.01) |
| *C12N 9/22* | (2006.01) |
| *C12N 15/11* | (2006.01) |
| *B33Y 80/00* | (2015.01) |

(52) U.S. Cl.
CPC ...... *G05B 19/4099* (2013.01); *A61L 27/3804* (2013.01); *A61L 27/3834* (2013.01); *B01L 3/502753* (2013.01); *B33Y 10/00* (2014.12); *B33Y 30/00* (2014.12); *B33Y 50/02* (2014.12); *B33Y 70/00* (2014.12); *C12M 21/08* (2013.01); *C12M 23/16* (2013.01); *C12N 5/0062* (2013.01); *C12N 5/0686* (2013.01); *C12N 5/0696* (2013.01); *C12N 5/0697* (2013.01); *C12N 9/22* (2013.01); *C12N 15/11* (2013.01); *B01L 2200/0652* (2013.01); *B33Y 80/00* (2014.12); *C12N 2310/20* (2017.05); *C12N 2510/00* (2013.01); *C12N 2513/00* (2013.01); *C12N 2800/80* (2013.01); *G05B 2219/49023* (2013.01)

(58) Field of Classification Search
CPC ...... G05B 19/4099; G05B 2219/49023; G05B 19/4097; G05B 19/418; B33Y 10/00; B33Y 30/00; B33Y 50/02; B33Y 70/00; B33Y 80/00; B33Y 50/00; A61L 27/3804; A61L 27/3834; B01L 3/502753; B01L 2200/0652; C12M 21/08; C12M 23/16; C12N 5/0062; C12N 5/0686; C12N 5/0696; C12N 5/0697; C12N 9/22; C12N 15/11; C12N 2310/20; C12N 2510/00; C12N 2513/00; C12N 2800/80; B29C 64/209; B29C 64/106; B29L 2031/7532
See application file for complete search history.

(56) References Cited

U.S. PATENT DOCUMENTS

| | | |
|---|---|---|
| 6,897,941 B2 | 5/2005 | Almogy |
| 7,513,822 B2 | 4/2009 | Flitsch |
| 7,733,364 B2 | 6/2010 | Nomura et al. |
| 8,229,585 B2 | 7/2012 | Flitsch |
| 8,300,076 B2 | 10/2012 | Nomura et al. |
| 8,982,275 B2 | 3/2015 | Suenobu |
| 9,059,227 B2 | 6/2015 | Flitsch |
| 9,171,697 B2 | 10/2015 | Flitsch |
| 9,558,915 B2 | 1/2017 | Flitsch |
| 2011/0169193 A1 | 7/2011 | Bonassar et al. |
| 2015/0301524 A1 | 10/2015 | Flitsch |
| 2016/0046078 A1 | 2/2016 | Sun et al. |
| 2016/0136895 A1 | 5/2016 | Beyer et al. |
| 2018/0025884 A1 | 1/2018 | Flitsch et al. |

*Primary Examiner* — Titilayo Moloye

(57) ABSTRACT

The present invention provides apparatus and methods for production of tissue structures and organs. In some examples, a cleanspace facility may be equipped with modelling hardware and software, nanotechnology and microelectronic apparatus, and additive manufacturing equipment to print cells and support matrix to allow cells to grow into tissue structures and organs. Various methods relating to using and producing the tissue engineering system are discussed.

20 Claims, 19 Drawing Sheets

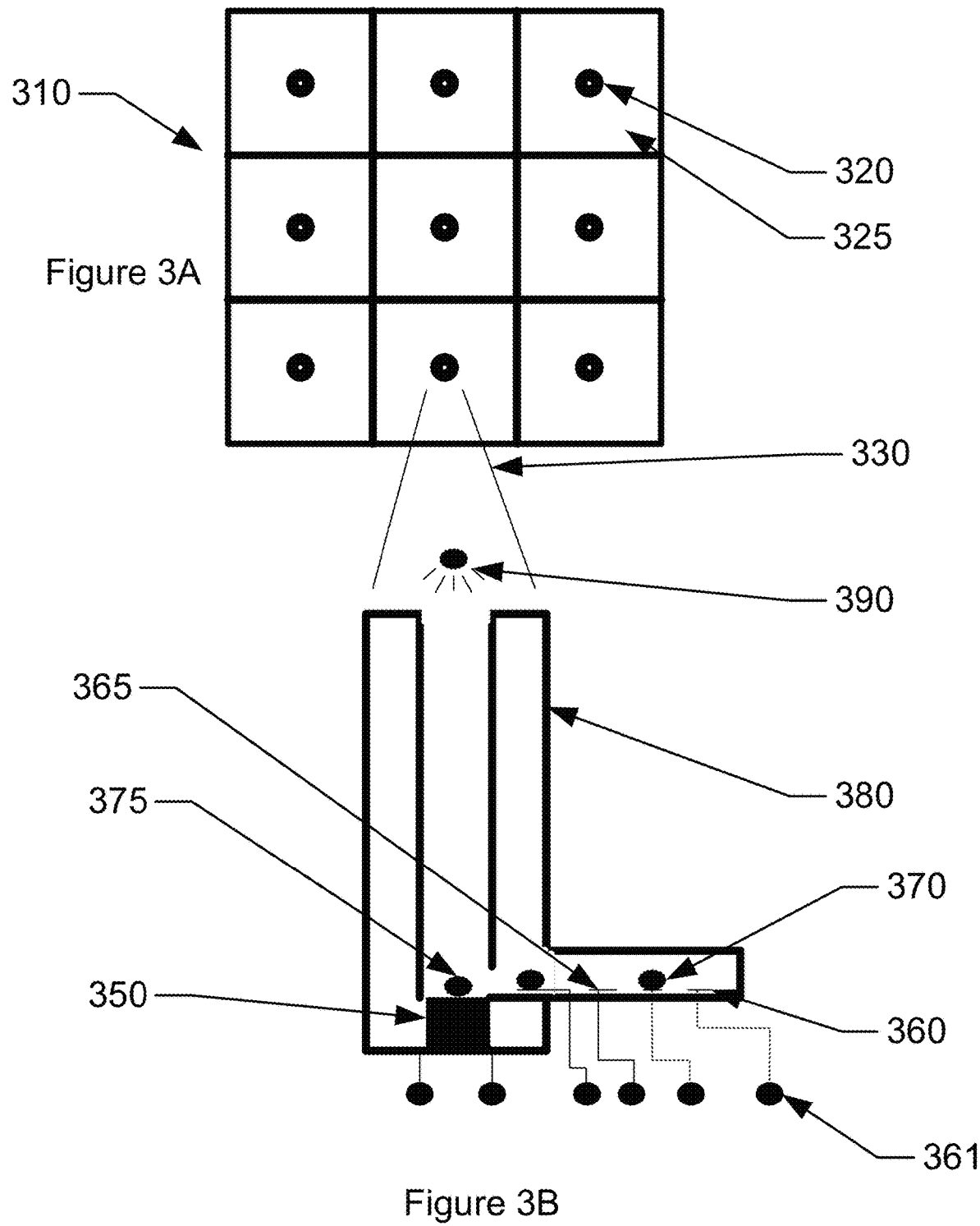

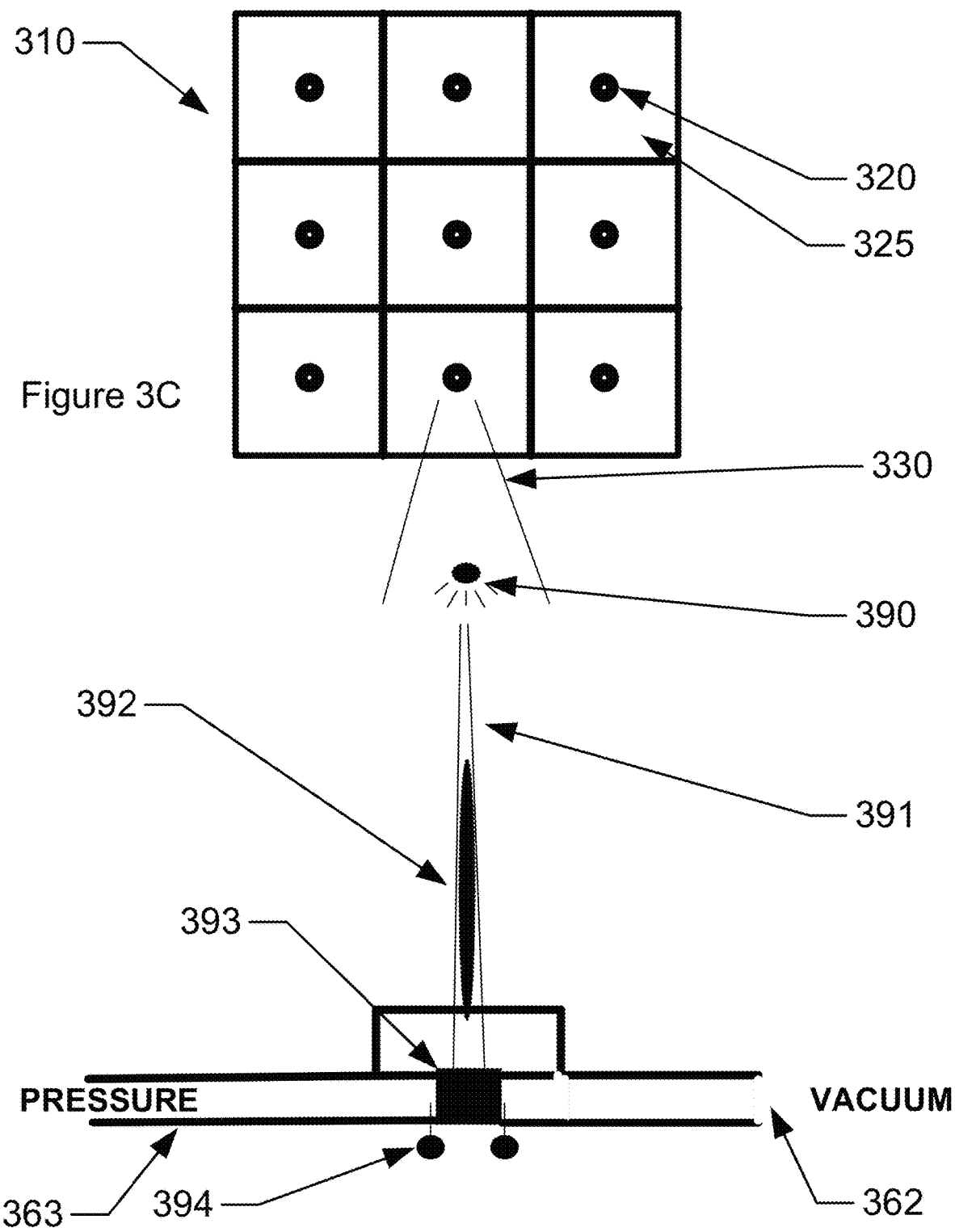

| | |
|---|---|
| 1210 | Assemble a collection of process tools into a manufacturing line |

↓

| | |
|---|---|
| 1220 | Perform measurements on a patient |

↓

| | |
|---|---|
| 1225 | Study patient's genome |

↓

| | |
|---|---|
| 1230 | Obtain samples of cells from patient |

↓

| | |
|---|---|
| 1235 | Optionally genetically modify cells |

↓

| | |
|---|---|
| 1240 | Form population of cells |

↓

| | |
|---|---|
| 1245 | Perform an analysis on the patient metrics and databases related to tissue structure and function |

Fig 12A

```
1250 → Create physical model of tissue or organ at imaging resolution
1251 → Optionally create or supplement the model of tissue or organ
1255 → Subject fabricator environment to sterilization
1260 → Deliver cells to the sterilized environment
1265 → Optionally build a model-based scaffold
1270 → Print different cell types based on model direction
1275 → Optionally Imprint nutritive layers
```

Fig 12B

METHOD AND APPARATUS FOR A TISSUE ENGINEERING SYSTEM

CROSS REFERENCE TO RELATED APPLICATION

This application is the national stage filing of U.S. PCT Application S/N PCT/US2018/35984 which in turn claims the benefit of the U.S. Provisional Application Ser. No. 62/515,983 filed on Jun. 6, 2017. The contents of each are hereby incorporated by reference.

FIELD OF THE INVENTION

The present invention relates to methods and associated apparatus and methods which relate to fabrication systems, processing tools and modeling systems and protocols used to create tissue layers on substrates and organs. Arrays of multiple chemical species printing elements or cell printing elements may be combined with microfluidic processors and other techniques to form a tissue processing system.

BACKGROUND OF THE INVENTION

A cleanspace fabricator can create an environment that supports complex material processing in a simple clean environment that is also very sterile. In some examples, people are not located within the primary cleanspace of a cleanspace fabricator. Therefore, their cellular matter, and its associated DNA may be isolated as a contaminant for materials that are being processed in the cleanspace fabricator. There are many different processes that may be performed in a cleanspace fabricator which may benefit from the sterile and clean environment that it affords.

Furthermore, there are numerous types of apparatus that may be created in a cleanspace environment such as the processing of microfluidic processing elements. Microfluidic processing elements may therefore be processed in a cleanspace fabricator and then be used in that cleanspace fabricator to perform processing themselves; leveraging the clean, genetically isolated and sterile aspects of the environment.

In nature, there are complex structures such as living tissues and organs that could be replicated or produced using technologies that could be efficiently operated within a cleanspace fabricator. The production of living tissues and organs could provide numerous benefits to medical needs of various kinds and to the field of regenerative medicine for example.

A medical environment is an ideal place to study a patient with a medical imaging technique to determine shape, function, and abnormalities about various tissues and organ structures within a patient. The same environment is also an ideal place to extract tissue samples from a patient. A cleanspace facility could be figured to support operations within such a medical environment. In a clean and sterile environment, cells from tissue samples may be isolated and induced to grow into stockpiles of cells.

Therefore, it would be very useful to create an environment that is sterile and well controlled, that may house and support equipment for the production of engineered tissues and organs. This may be especially useful if the cell stock that is used for the production of the engineered tissues and organs originates from a patient that requires the tissues or organs. Finally, it would also be useful if the information of medical imaging studies may be compiled to created models for the formation of the engineered tissues.

SUMMARY OF THE INVENTION

Accordingly, methods and apparatus for a tissue engineering system based on these principles are described herein. And, the present invention provides apparatus and methods to create tissue layers on substrates and to create organs within a tissue engineering system that may be located within a cleanspace fabricator. Massively parallel implementations of chemical species printing elements or cell printing elements may be combined with other techniques to form a tissue processing system.

The present invention may utilize modelling techniques to incorporate medical imaging data as well as functional knowledge of organs, tissue, and structure. In some examples, a model will calculate structures based on mathematical constructs, such as fractal equations, with constraints defined in other parts of the model and forms. The models may be used to form structure with techniques including photolithography, reactive ion etching, chemical etching, film deposition, additive manufacturing and the like. The models may be used to detail locations to print different cell types, or different molecules which may attract different cell types to a location. In still further examples, the models may be used to print chemical and biochemical deposits that maybe used to direct differentiation of various pluripotent or omnipotent stems cells to form differentiated cell types.

In some embodiments the tissue systems may be used in conjunction with cleanspace fabricators. Cleanspace fabrication facilities have been defined in various patent specifications, and the teachings and definition of these published specification may form a basis for understanding the utility of the inventive art herein within cleanspace environments.

The present invention also provides novel methods of utilizing these designs for processing fabs which rearrange the clean room into a cleanspace and thereby allow processing tools to reside in both vertical and horizontal dimensions relative to each other and in some embodiments with their tool bodies outside of, or on the periphery of, a clean space of the fabricator. In such a design, the tool bodies can be removed and replaced with much greater ease than is the standard case. The design also anticipates the automated transfer of substrates inside a clean space from a tool port of one tool to another. The substrates can reside inside specialized carriers designed to combinations of substrates which may be coordinated to form organs. The cleanspace fabricator may enhance the ability to keep the environment of cell growth antiseptic, sterile and otherwise clean. The isolation of material from human works also aids in keeping genetic integrity of the cell lines that are growing.

Further design enhancements can entail the use of automated equipment to carry and support tools such as printing tools in their movement into and out of the fab environment and into and out of organ growth locations. In this invention, numerous methods of using some or all of these innovations in designing, operating or otherwise interacting with such fabricator environments are described. The present invention can therefore include methods and apparatus for situating processing tools in a vertical dimension and control software modules for making such tools functional both within the cleanspace entity itself and also in networks of such fabricators wherein at least one of the processing tools incorporates an imaging system comprised of a multitude of imaging elements.

A cleanspace fabricator with the various tools described herein may be located within hospitals and medical organizations. Proximity to operating rooms may allow for optimal conditions of sterility and minimal impacts of times between when the tissue is in nourishing conditions and when it is isolated.

One general aspect includes a method of forming a tissue layer including: configuring a tissue engineering apparatus which includes a cleanspace fabricator, where the cleanspace fabricator is configured to process at least a first substrate including tissue layers, where the cleanspace fabricator maintains both a particulate cleanliness as well as a biological sterility cleanliness, where the cleanspace fabricator includes at least a first processing apparatus and a second processing apparatus deployed along a periphery of the cleanspace fabricator, and where the cleanspace fabricator includes automation to move one or more of the first substrate and the first processing apparatus within a primary cleanspace of the cleanspace fabricator.

The cleanspace fabricator also may include a modelling system, where the modelling system is configured to produce a first digital model which is used to control at least the first processing apparatus, where the first processing apparatus controls equipment to create one or more of: a tissue support matrix and a printed deposit of cellular and molecular material.

The cleanspace fabricator also may include examples where a portion of the first processing apparatus includes a second substrate with a multitude of printing elements arrayed thereupon, where the multitude of printing elements are capable of emitting a fluid including at least a first cell to a region within the first processing apparatus based upon a final three-dimensional model.

The cleanspace fabricator also may include examples where the first processing apparatus further includes a microfluidic processing system to process cellular and chemical material and deliver a product to the multitude of printing elements.

The method also may include placing a first substrate within the cleanspace fabricator. The method also may include performing a medical imaging technique upon a patient. The method also may include creating the first digital model, where an input to the first digital model includes at least the results of the medical imaging technique. The method also may include refining the first digital model to create a final digital model, where the final digital model represents a three-dimensional model for depositing of cellular material and where the refining is performed by an algorithmic processing of the first digital model. The method also may include forming two or more individual printing system elements. The method also may include aligning the two or more individual printing system elements in space relative to the first substrate. The method also may include obtaining a tissue sample from the patient. The method also may include processing the tissue sample within the microfluidic processing system to create a first stock of cells, where the microfluidic processing system isolates cells of different cell types, and where the microfluidic processing system performs a genetic modification protocol on at least a cell from the tissue sample. The method also may include printing a tissue support matrix included of a gelled material, where the gelled material includes channels within its form through which fluids may flow, and where the gelled material is one or both of absorbable by a growing tissue in contact with the gelled material or dissolvable with fluids of the growing tissue or fluids flowed through the tissue support matrix. The method also may include printing cells from the first stock of cells into the gelled tissue support matrix using an array of micropipettes, where each of the micropipettes include sharp needles to penetrate the gelled material and to reach locations in three dimensionally accessible regions of the gelled tissue support matrix, and where the array of micropipettes uses location control signals that are based upon the final digital model.

Another general aspect includes a tissue engineering apparatus including: a cleanspace fabricator, where the cleanspace fabricator is configured to process at least a first substrate including tissue layers, where the cleanspace fabricator maintains both a particulate cleanliness as well as a biological sterility cleanliness, where the cleanspace fabricator includes at least a first processing apparatus and a second processing apparatus deployed along a periphery of the cleanspace fabricator, and where the cleanspace fabricator includes automation to move one or more of the first substrate and the first processing apparatus within a primary cleanspace of the cleanspace fabricator.

In some examples the cleanspace fabricator may include a modelling system, where the modelling system is configured to produce a first three dimensional model which is used to control at least the first processing apparatus, where the first processing apparatus controls equipment to create one or more of a tissue support matrix and a printed deposit of cellular and molecular material, and where the modelling system includes a first processor to perform algorithmic processes of machine learning upon an atlas of imaging data from one or more imaging modalities, and where the first processor further performs a generative design algorithm to synthesize one or more of at least a first unit element, a desired tissue construct and a structural goal into the first three dimensional model as a composite of a result of the machine learning processing of the atlas of imaging data and a result of the generative design algorithm.

In some implementations, the first processing apparatus includes a second substrate with a multitude of printing elements arrayed thereupon, where the multitude of printing elements are capable of emitting a fluid including at least a first cell to a region within the first processing apparatus based upon a final three dimensional model; and where the first processing apparatus further includes a microfluidic processing system to process cellular and chemical material and deliver a product to the multitude of printing elements.

Implementations may include one or more of the following features. The tissue engineering apparatus may further include examples where the final three-dimensional model is derived from the first three-dimensional model, and where an artificial intelligence algorithm adjusts the first three-dimensional model to create a new model that the artificial intelligence algorithm evaluates as more effective. This effectiveness may be measured across a set of evaluation metrics assessed by the artificial intelligence algorithm. In some examples, the adjustment of the first three-dimensional model may include steps involving interaction with human decision making.

The tissue engineering apparatus also may include examples where the printing elements are arranged into an array, and where the printing elements include individual micropipettes.

The tissue engineering apparatus may include examples where the gelled material creates an approximately neutral buoyancy environment for the printed deposit.

The tissue engineering apparatus may include examples where the individual micropipettes of the micropipette array are fastened to actuators that allow a degree of independent movement from the array as a whole.

The tissue engineering apparatus may include examples where the tissue engineering apparatus is capable of functioning in a micro-gravity environment.

BRIEF DESCRIPTION OF THE DRAWINGS

The accompanying drawings, that are incorporated in and constitute a part of this specification, illustrate several embodiments of the invention and, together with the description, serve to explain the principles of the invention:

FIGS. 3A-D—Exemplary depictions of an array of imaging elements and a close-up view of an exemplary small sized imaging element.

FIGS. 12A-C—An exemplary processing flow to produce tissue layers and/or organs.

DETAILED DESCRIPTION OF THE INVENTION

In patent disclosures by the same inventive entity, the innovation of the cleanspace fabricator has been described. In place of a cleanroom, fabricators of this type may be constructed with a cleanspace that contains the wafers, typically in containers, and the automation to move the wafers and containers around between ports of tools. The cleanspace may typically be much smaller than the space a typical cleanroom may occupy and may also be envisioned as being turned on its side. In some embodiments, the processing tools may be shrunk which changes the processing environment further.

Description of a Linear, Vertical Cleanspace Fabricator

There are a number of types of cleanspace fabricators that may be possible with different orientations. For the purposes of illustration, one exemplary embodiment includes an implementation with a fab shape that is planar with tools oriented in vertical orientations. An exemplary representation of what the internal structure of these types of fabs may look like is shown in a partial cross section representation in FIG. 1. Item 110 may represent the roof of such a fabricator where some of the roof has been removed to allow for a view into the internal structure. Additionally, items 120 may represent the external walls of the facility which are also removed in part to allow a view into external structure.

Figure 1:
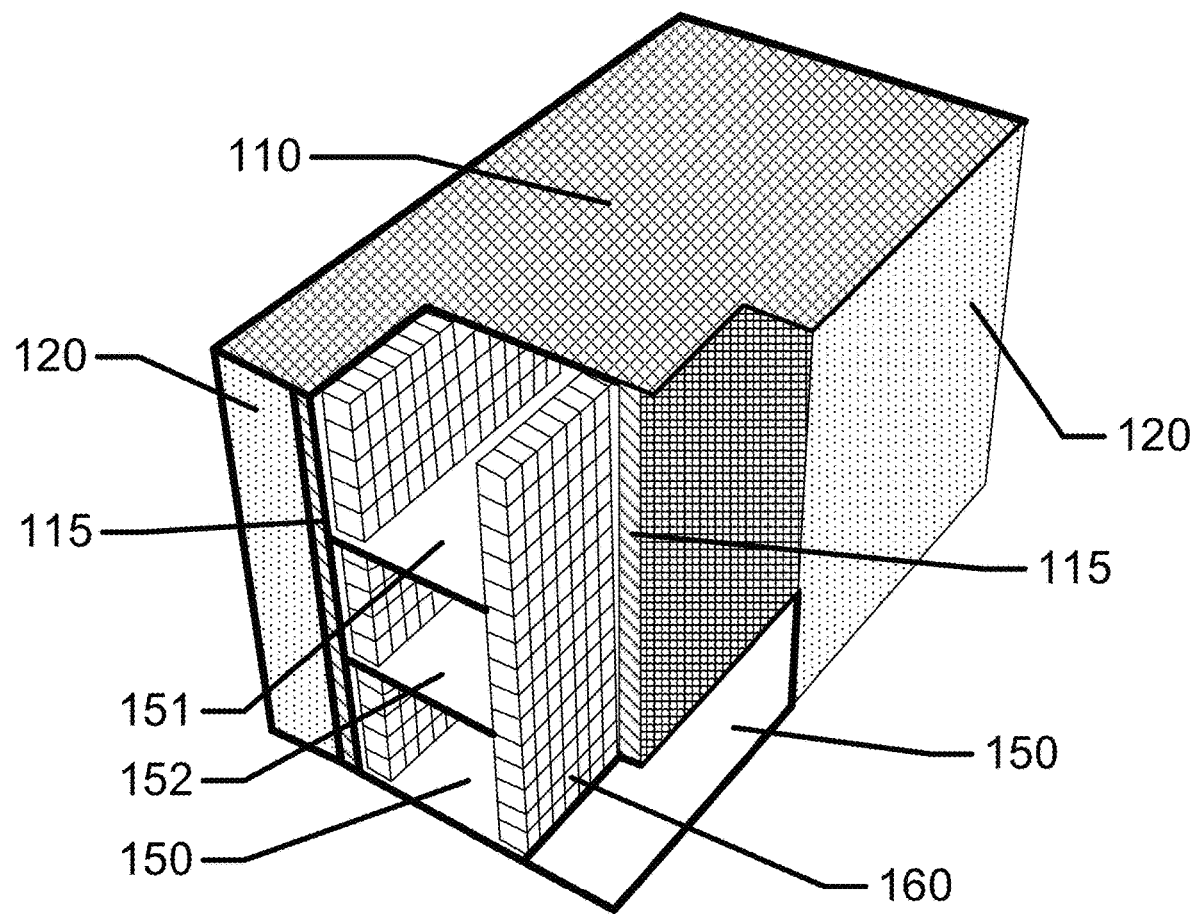
FIG. 1—An illustration of a small tool cleanspace fabricator in a sectional type representation.

In the linear and vertical cleanspace fabricator of FIG. 1 there are a number of aspects that may be observed in the representation. The "rotated and shrunken" cleanspace regions may be observed as cleanspace regions 115. The occurrence of cleanspace regions 115 on the right side of the figure is depicted with a portion of its length cut off to show its rough size in cross section. The cleanspaces lie adjacent to the tool pod locations. Depicted as item 160, the small cubical features represent tooling locations within the fabricator. These locations are located vertically and are adjacent to the cleanspace regions (115). In some embodiments a portion of the tool, the tool port, may protrude into the cleanspace region to interact with the automation that may reside in this region.

Floor 150 may represent the fabricator floor or ground level. On the right side, portions of the fabricator support structure may be removed so that the section may be demonstrated. In between the tools and the cleanspace regions, the location of the floor 150 may represent the region where access is made to place and replace tooling. In some embodiment, as in the one in FIG. 1, there may be two additional floors that are depicted as items 151 and 152. Other embodiments may have now flooring levels and access to the tools is made either by elevator means or by robotic automation that may be suspended from the ceiling of the fabricator or supported by the ground floor and allow for the automated removal, placement and replacement of tooling in the fabricator.

Description of a Chassis and a toolPod or a Removable Tool Component

In other patent descriptions of this inventive entity (patent application Ser. No. 11/502,689 which is incorporated in its entirety for reference) description has been made of the nature of the toolPod innovation and the toolPod's chassis innovation. These constructs, which in some embodiments may be ideal for smaller tool form factors, allow for the easy replacement and removal of the processing tools. Fundamentally, the toolPod may represent a portion or an entirety of a processing tool's body. In cases where it may represent a portion, there may be multiple regions of a tool that individually may be removable. In either event, during a removal process the tool may be configured to allow for the disconnection of the toolPod from the fabricator environment, both for aspects of handling of product substrates and for the connection to utilities of a fabricator including gasses, chemicals, electrical interconnections and communication interconnections to mention a few. The toolPod represents a stand-alone entity that may be shipped from location to location for repair, manufacture, or other purposes.

Imaging Apparatus

Figure 2:
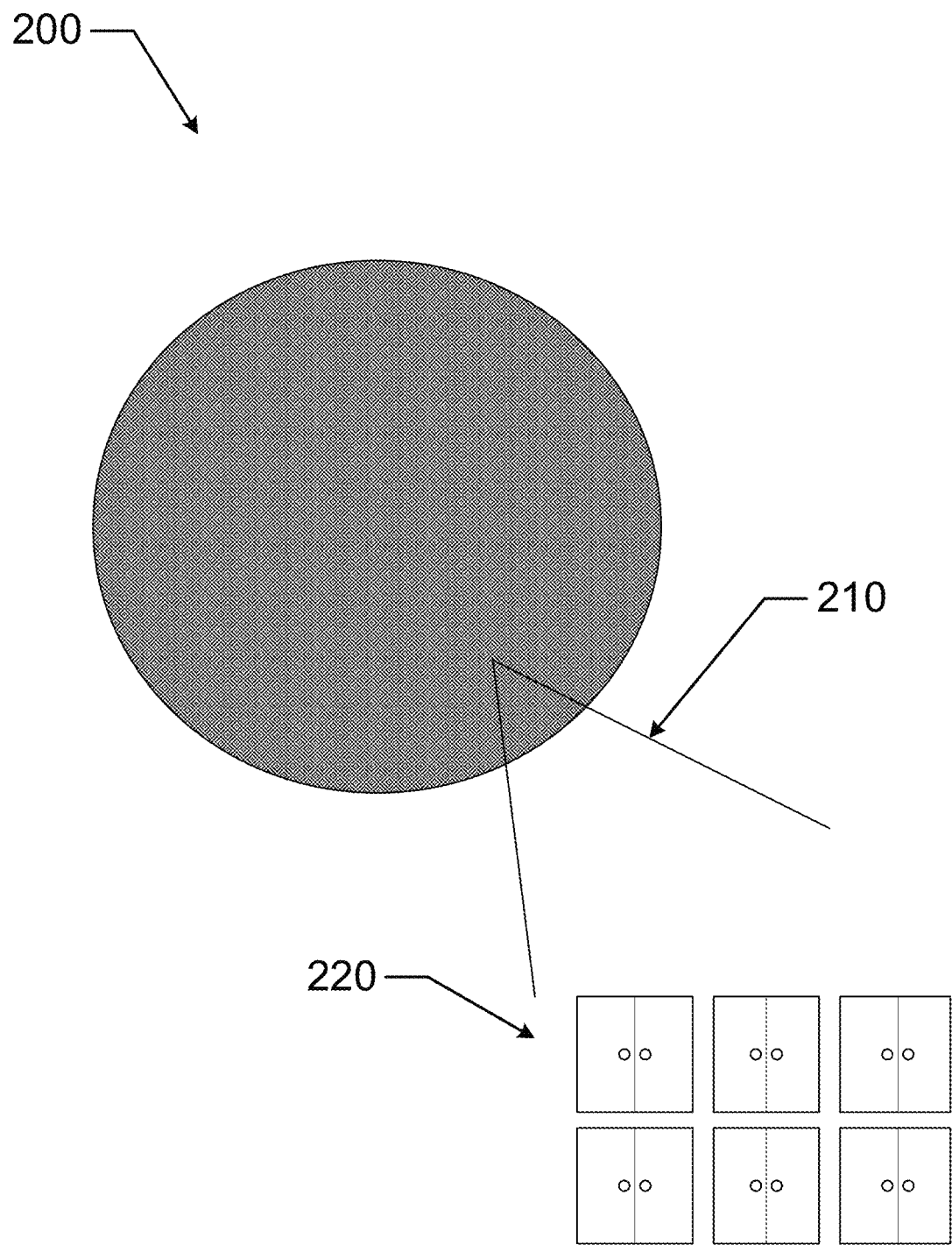
FIG. 2—An illustration of a full substrate imaging apparatus with highlighted regions illustrated at higher scale to depict a collection of individual imaging elements.

An imaging apparatus of various types may be used in the various cleanspace fabricator designs that have been described herein and in other referenced applications. Referring to FIG. 2 at item 200 an exemplary imaging apparatus in the exemplary form factor of a round substrate is depicted. In some embodiments, the imaging apparatus may be comprised of a large number of similar elements. As shown in a magnified view 210, the individual elements may be arranged in a regular pattern 220.

Referring to FIG. 3A at a close up of an imaging element may be depicted in cross section and FIG. 3B a plan view. A type of micro imaging element may be found in reference to FIGS. 3A and 3B. At 3A, item 310, an exemplary array of nine elements such as 325 with an associated image element 320 may be found. One of the elements represented in the close-up 330 of FIG. 3B may be found. This element may be useful for ejecting nanoscale droplets of chemical reactant to react with resist layers to form imaged layers. Item 390 may be an ejected droplet which may contain chemicals, cells or both chemicals and cells. Item 380 may be an element to eject a droplet 375. A piezoelectric element 350 may be useful as such an ejection element or other such features as may be found in ink jet printing technology may be represented by 350. At 370 droplets may be moved by microfluidic techniques through the use of coated electrodes such as items 360 and 365. The electrodes may receive electrical control signals through interconnects from controlling systems. An example of such an electrical connect is depicted at 361.

In some alternative examples, referring to FIGS. 3C and 3D, an array with the same feature aspects such the array 310, element 325 with imaging element 320. In this example, the close-up 330 shows a droplet 390 emerging from a pipet head 391. Pipets can be used to draw up material to be ejected 392. A switch 393, can open the pipet to vacuum 363 to draw material into the pipet and may switch to a pressure 362 situation under activation from electrical contacts 394. The illustration shows an array of 9 elements, however much larger arrays may be built. The pipets may be located into reservoirs containing the material to be distributed. Large channels may receive numerous pipets simultaneously. The pipets may collect a small enough volume of material that a single cell may occupy the pipet. In some examples, an optical detection system may observe the droplet in the pipet to determine the presence of a single cell in the pipette. In some examples, the pipette reservoir may be filled from an external port connecting to the reservoir of the pipet. Such an external port may need to close when the pipette is pressurized to distribute its contents. The imaging array may be moved along various coordinate systems including non-limiting examples of cartesian, polar, cylindrical, spherical and other such coordinate systems. By moving the imaging elements in space, deposits may be created in three dimensions.

Methods of Producing and Utilizing Imaging Systems

Figure 4:
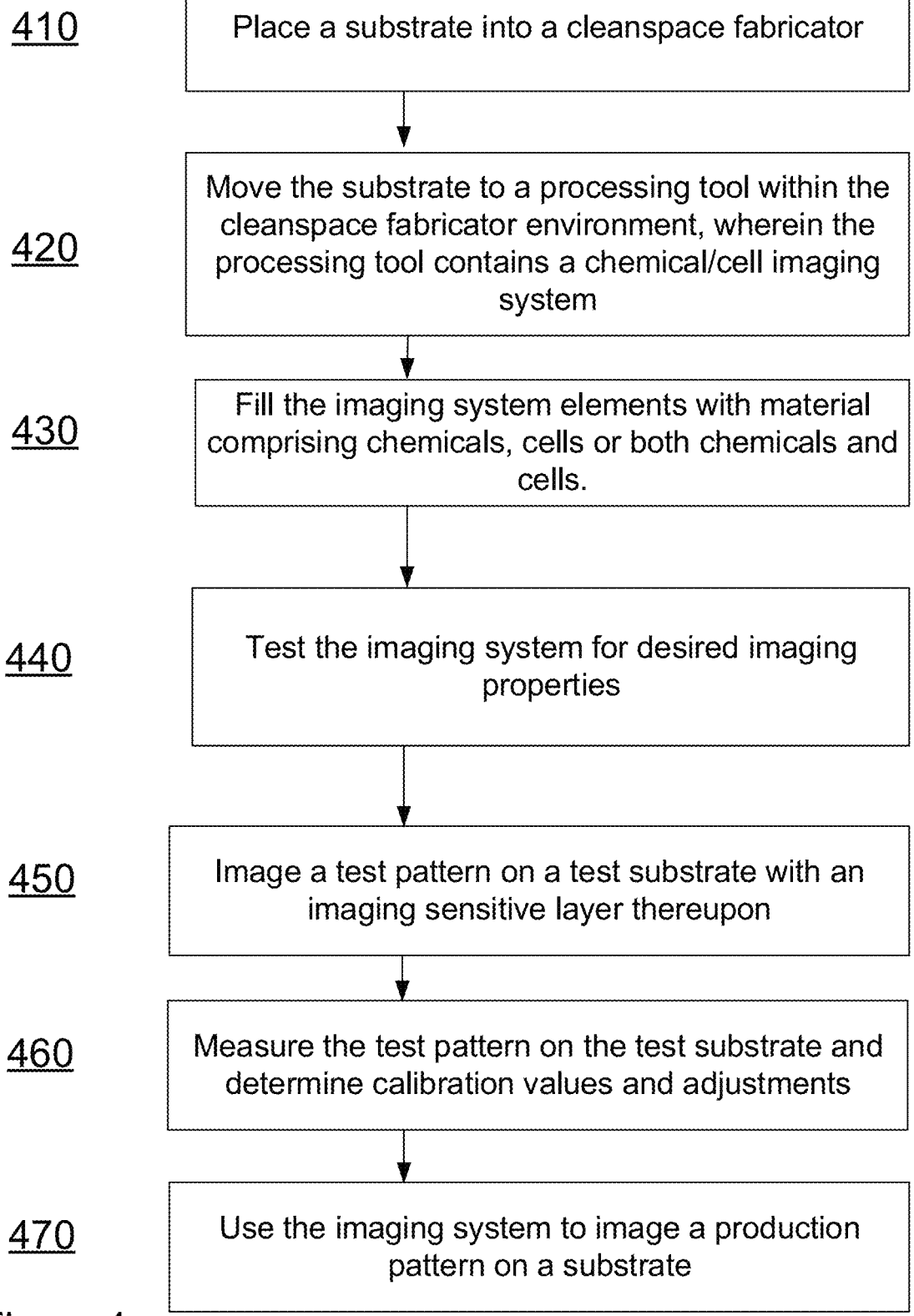
FIG. 4—A Flow chart depicting exemplary methods of production of an imaging apparatus.

Referring to FIG. 4, a method for producing an imaging system may be found. At Step 410, a substrate may be placed within a cleanspace fabricator. At step 420 the substrate may be moved to a processing tool. In some embodiments, the processing tool may be located within a toolPod. At step 430 a processing step may be performed within the processing tool as part of a processing flow to form an imaging system. At step 440, the imaging components upon the substrate may be tested for their desired imaging properties. At step 450, the imaging system may be used to image a test pattern on a substrate with an imaging sensitive layer thereupon. At 460, a metrology process may be performed on the substrate with the test pattern and calibration adjustments may be determined. At 470 the imaging system may be used to image a production pattern on a substrate with an imaging sensitive layer thereupon.

Control Systems

Figure 5:
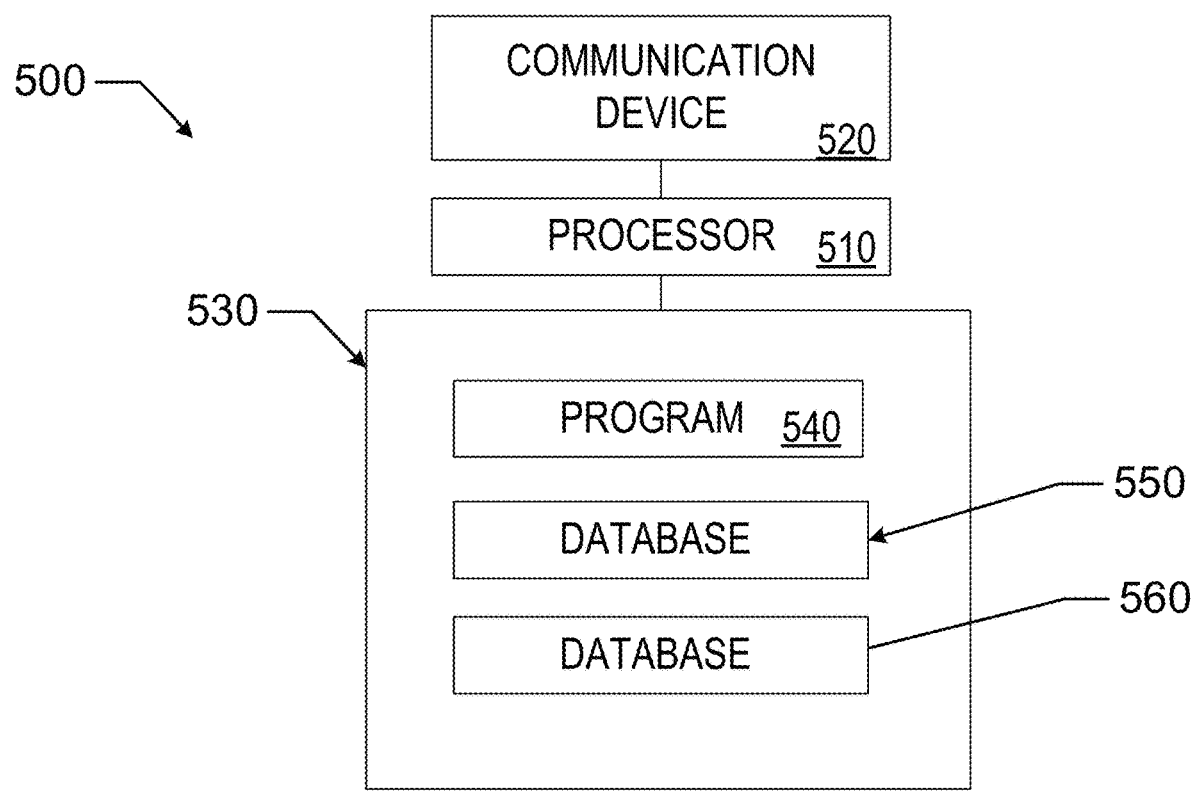
FIG. 5—An exemplary processor that may be useful for some embodiments of imaging systems.

Referring now to FIG. 5, a controller 500 is illustrated that may be used in some embodiments of an imaging system. The controller 500 includes a processor 510, which may include one or more processor components. The processor may be coupled to a communication device 520.

The processor 510 may also be in communication with a storage device 530. The storage device 530 may comprise a number of appropriate information storage device types, including combinations of magnetic storage devices including hard disk drives, optical storage devices, and/or semiconductor memory devices such as Flash memory devices, Random Access Memory (RAM) devices and Read Only Memory (ROM) devices.

At 530, the storage device 530 may store a program 540 which may be useful for controlling the processor 510. The processor 510 performs instructions of the program 540 which may affect numerous algorithmic processes and thereby operates in accordance with imaging system manufacturing equipment. The storage device 530 can also store imaging system related data, including in a non-limiting sense imaging system calibration data and image data to be imaged with the imaging system. The data may be stored in one or more databases 550, 560. The databases 550, 560 may include specific control logic for controlling the imaging elements which may be organized in matrices, arrays, or other collections to form a portion of an imaging manufacturing system.

Cell Printing

In some examples, the multiple print head devices as have been described may be used to print single cells upon a substrate. in some examples, a droplet containing a cell in a liquid media, such as growth media, may be printed. In some other examples, the cell may be printed alone. There may be numerous types of cells that may be printed at different locations determined by a model used to control the print head. The different cells may be grown from stem cell parents obtained or created from cellular material of a patient. Through various means, the stem cells may be differentiated and grown up to larger volumes of cells for printing. The multiple print heads may be fed in channels that form a row of print heads. In other examples, each print head may be positioned with its own reservoir that may contain a sample of cells for that print head alone. The print heads may be fed by reservoirs and piping and pipetting systems, or in some examples the print head may be married to a microfluidic processing element that may allow material to be distributed to any of the means of distribution to the print heads.

Stem Cells and Biochemical Processing for Differentiation

In some examples, a large print head with many individual printing element, such as over 10,000 for example, may be used to print relatively large areas with cells of different types to form tissues with the deposition. In a non-limiting example, cells to be printed may be cells of an individual patient, where the printed cells are grown from a cell line that originates with the patient him/herself.

Figure 6:
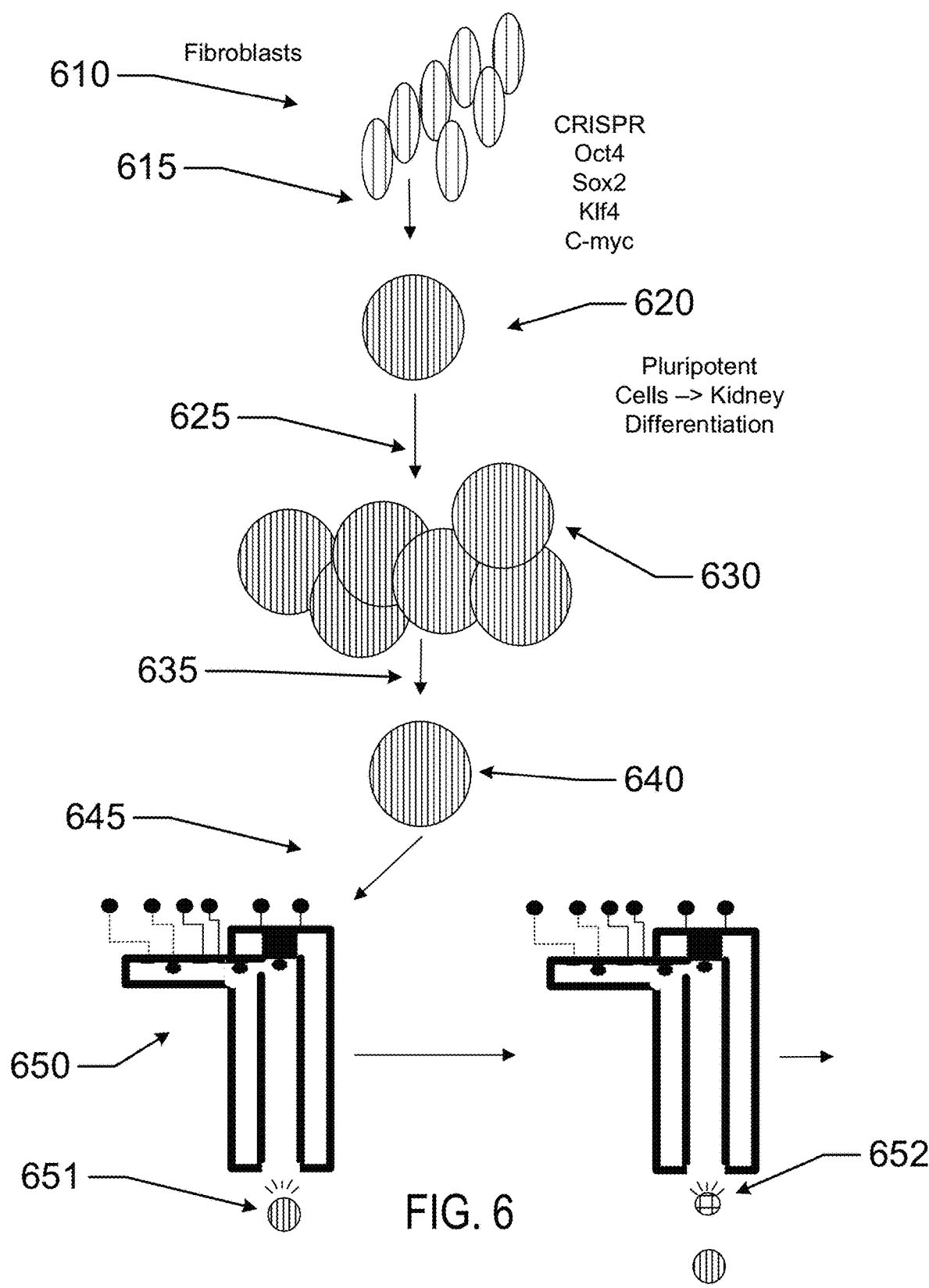
FIG. 6—An exemplary processing flow for printing of cells.

Referring to FIG. 6, an example of printing cells from a patient is illustrated. A sample of cells may be obtained from the patient such as the exemplary fibroblast cells 610 which may be isolated from a sample of a patient's skin. There may be numerous manners to induce the sample cells to become stem cells which will have the potential to grow and multiply. In a non-limiting example, genetic modification of the fibroblast cells may be performed. In an example, a transcription technique or gene editing technique 615 such as those based on CRISPR-Cas9 may be used to induce alteration of a series of genes such as the OCT4, SOX2, KLF4 and C-MYC genes which have been shown to induce pluripotency. The pluripotent cells 620 may be grown up and multiplied 625 to a collection of pluripotent kidney cells 630. In some examples, the growing collection of cells may be dissociated by physical or chemical means and separated 635. In some examples, separation of any cells that are not pluripotent may be accorded by the binding of antibodies to the cells that differentiate the different cell types. The different cells some with bound antibodies which may have a fluorescent marker attached or may be a substrate for an additional antibody that has a fluorescent marker may be sorted based on the fluorescent signals of the antibodies or other dyes. The separated individual pluripotent cells 640 may be loaded or passed 645 into the printing system. A printing system of the type herein may print 650 the cell 651 either in a droplet of media or by itself at a location that is determined by an algorithm that processes a model of the location of various cell types. In some examples, another material may be printed after the cell is printed. This additional material may include the addition of recombinant growth factors or small agonists 652 that may guide the pluripotent stem cell to differentiate into a desired type of cell for the location.

Figure 7:
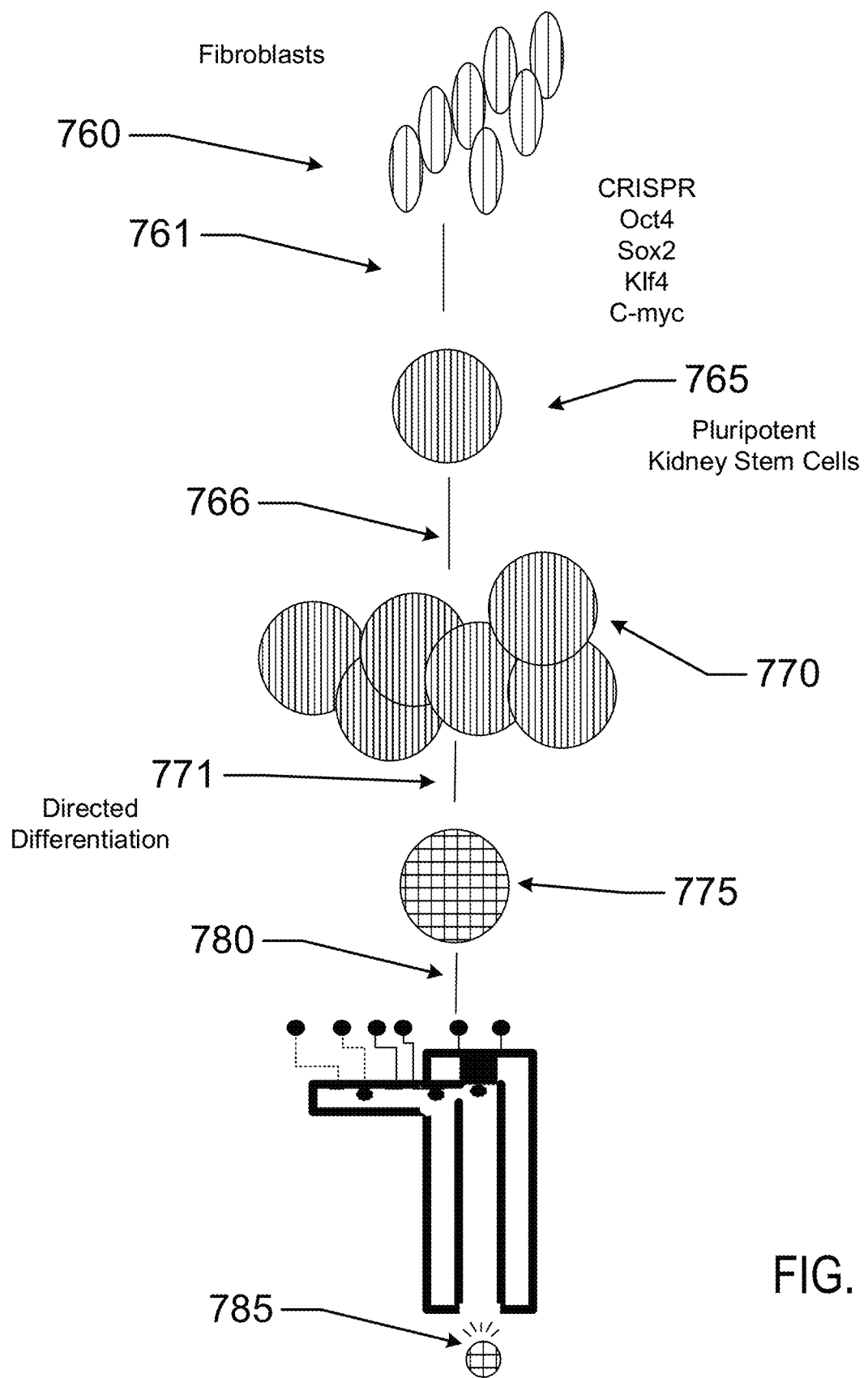
FIG. 7—An alternative exemplary processing flow for the printing of cells.
Figure 8:
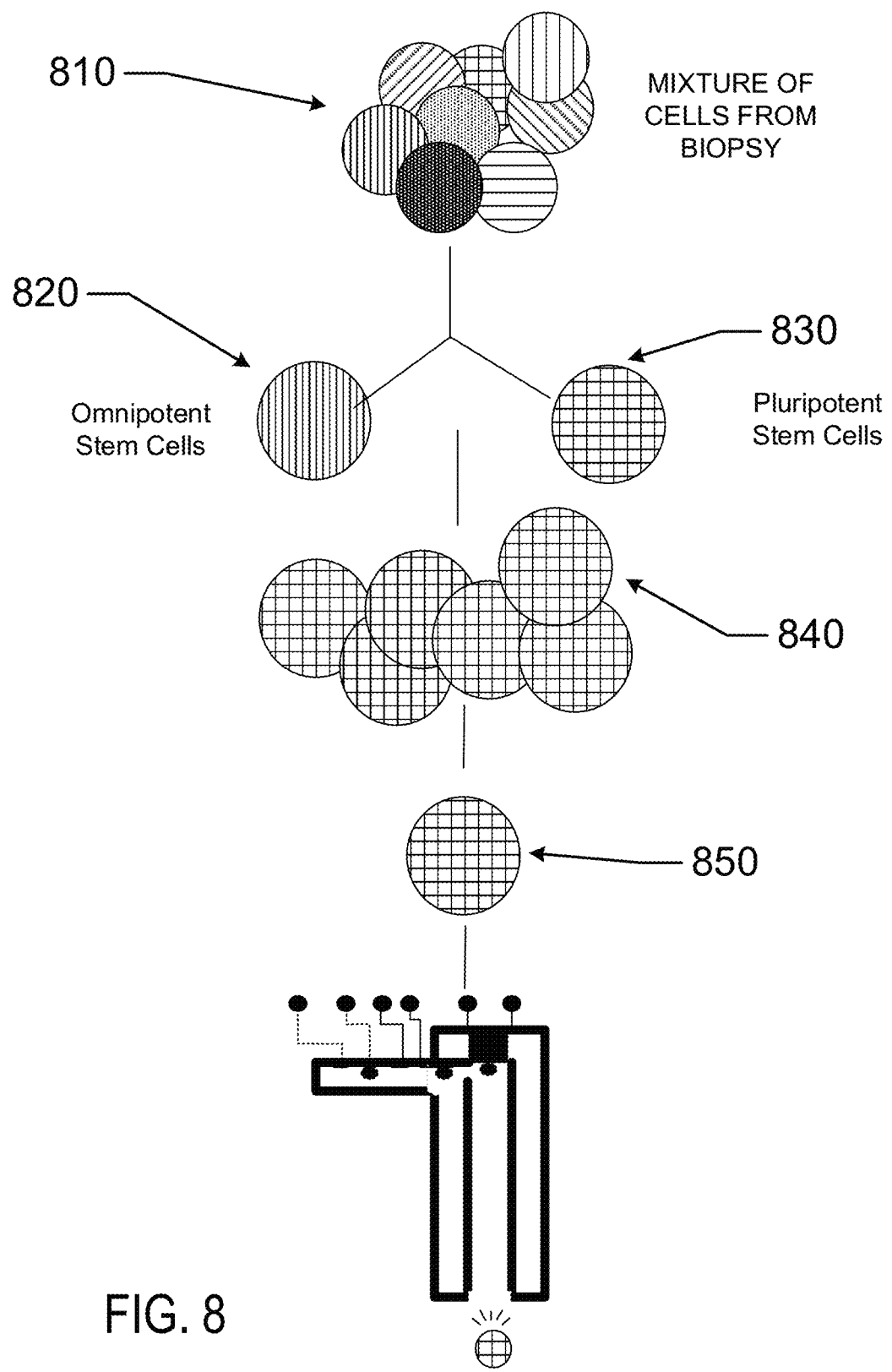
FIG. 8—An alternative exemplary processing flow for the printing of cells.

Referring to FIG. 7, a different printing scheme may be observed. A sample of cells may be obtained from the patient such as the exemplary fibroblast cells 760 which may be isolated from a sample of a patient's skin. There may be numerous manners to induce the sample cells to become stem cells which will have the potential to grow and multiply. In a non-limiting example, genetic modification of the fibroblast cells may be performed. In an example, a transcription technique or gene editing technique 761 such as those based on CRISPR-Cas9 may be used to induce alteration of a series of genes such as the OCT4, SOX2, KLF4 and C-MYC genes which have been shown to induce pluripotency. The pluripotent cells 765 may be grown up 766 to a population 770 and then influenced with the addition of recombinant growth factors or small agonists 771 to differentiate into various Kidney cell types 775. In some examples, the Kidney type differentiated cells can form embryonic forms of key Kidney elements including the nephron and early stage elements including the glomerulus and the urinary system. In some examples, the growing elements may be dissociated by physical or chemical means and separated. In some examples, separation may be accorded by the binding of antibodies to the cells that differentiate the different cell types and may be sorted based on the fluorescent signals of the antibodies or other dyes. Other separation schemes may be employed. The separated individual cell types 775 may be loaded or passed 780 into the printing system. A printing system of the type herein may print 785 the cell either in a droplet of media or by itself at a location that is determined by an algorithm that processes a model of the location of various cell types. In some examples, another material may be printed after the cell is printed Other organ types or tissue types may be processed in analogous means. The examples relating to kidney cells are just one of many examples which may include skin, bone, heart, liver, colon, thyroid, brain, muscle, and other types. Referring to FIG. 8 an alternative method of printing cells is illustrated. A mixture of cells may be collected from a biopsy 810 of a patient. In some examples, the biopsy may include a small number of stem type cells. In some examples, which may be very rare, omnipotent stem cells 820 may be found. Such cells could be used for printing schemes. In other examples, pluripotent stem cells may be located within portions of an associated organ, such as kidney pluripotent stem cells 830. These pluripotent stem cells 830 may be grown up and multiplied 840. In some examples, the growing collection of cells may be dissociated by physical or chemical means and separated. In some examples, separation of any cells that are not pluripotent may be accorded by the binding of antibodies to the cells that differentiate the different cell types. The different cells some with bound antibodies which may have a fluorescent marker attached or may be a substrate for an additional antibody that has a fluorescent marker may be sorted based on the fluorescent signals of the antibodies or other dyes. The separated individual pluripotent cells 850 may be loaded or passed into the printing system. A printing system of the type herein may print the cell either in a droplet of media or by itself at a location that is determined by an algorithm that processes a model of the location of various cell types. In some examples, another material may be printed after the cell is printed. This additional material may include the addition of recombinant growth factors or small agonists that may guide the pluripotent stem cell to differentiate into a desired type of cell for the location.

Printing Tissue Films with Multiple Cell Types with Chemical Imaging System

Figure 9A:
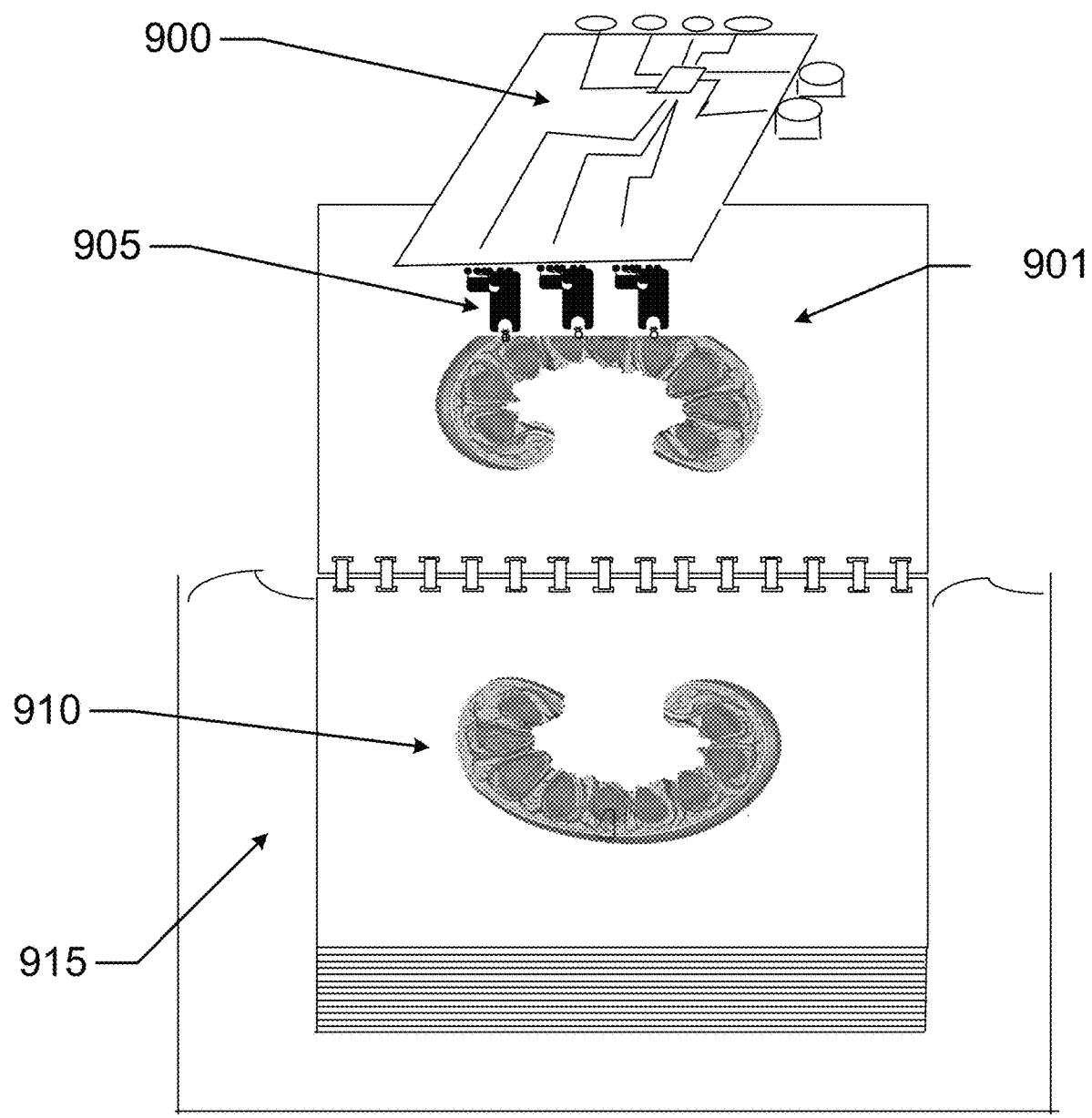
FIGS. 9A-D—An exemplary processing flow to produce a kidney organ.

Referring to FIG. 9A, a method to print tissue layers using the concepts discussed herein is illustrated. A microfluidic processor with attached printing array element 900 is illustrated processing a flat substrate 901 to print 905 on tissue layers. The substrate may be formed of a variety of materials. In some examples, the substrate may be formed of biomaterials such as collagen or collagen related materials. In other examples resorbable materials from synthetic materials may be used. In some examples, the substrate may be processed to remove regions of the body of the sheet. Onto the substrate, cells may be printed resulting in a tissue layer 910 that may be stored in a nourishing medium 915. The cells may grow from the locations that they were printed in. Depending on the resolution of the printing system, small features may not be able to be imaged by the printing means.

Figure 9B:
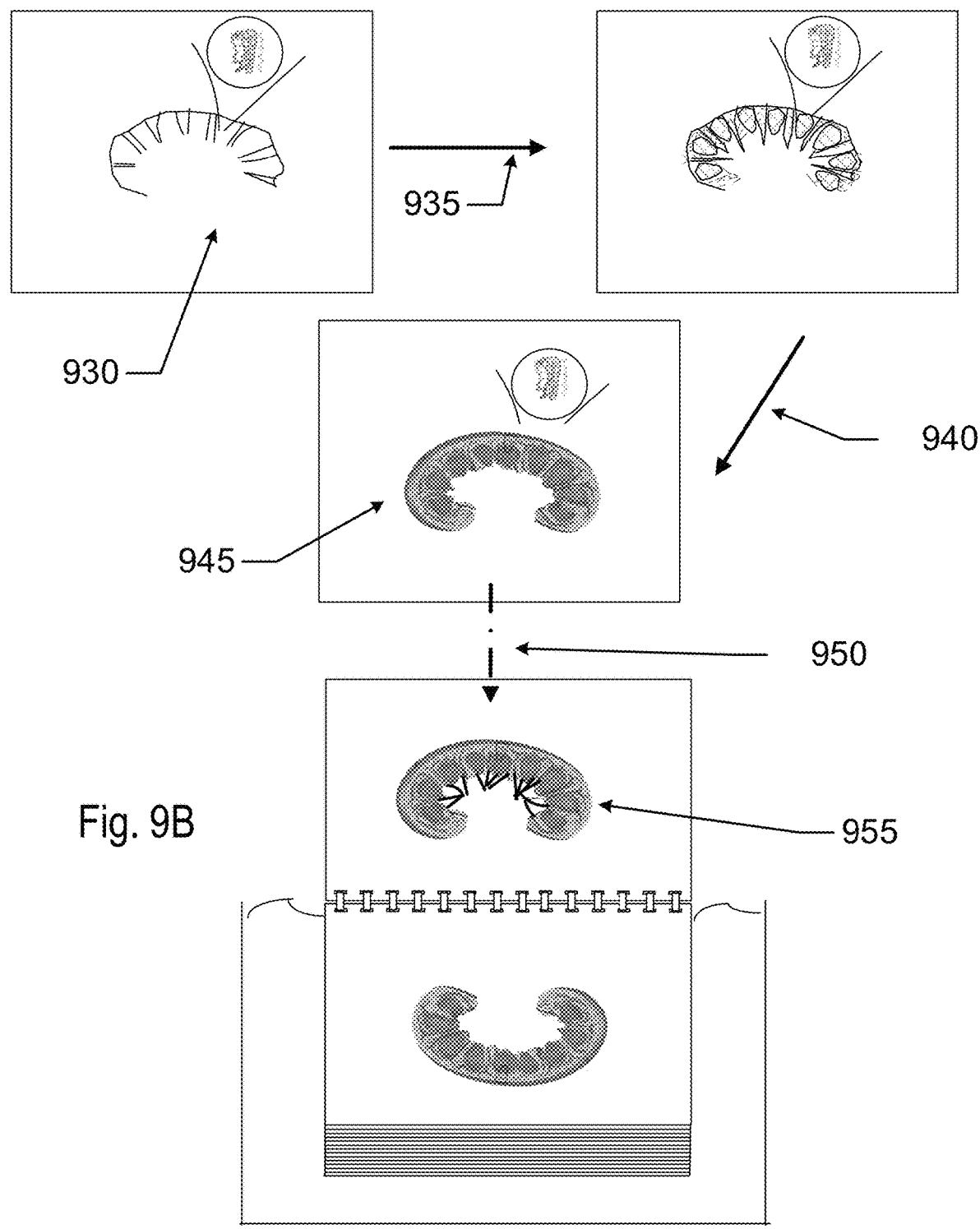
Figure 9C:
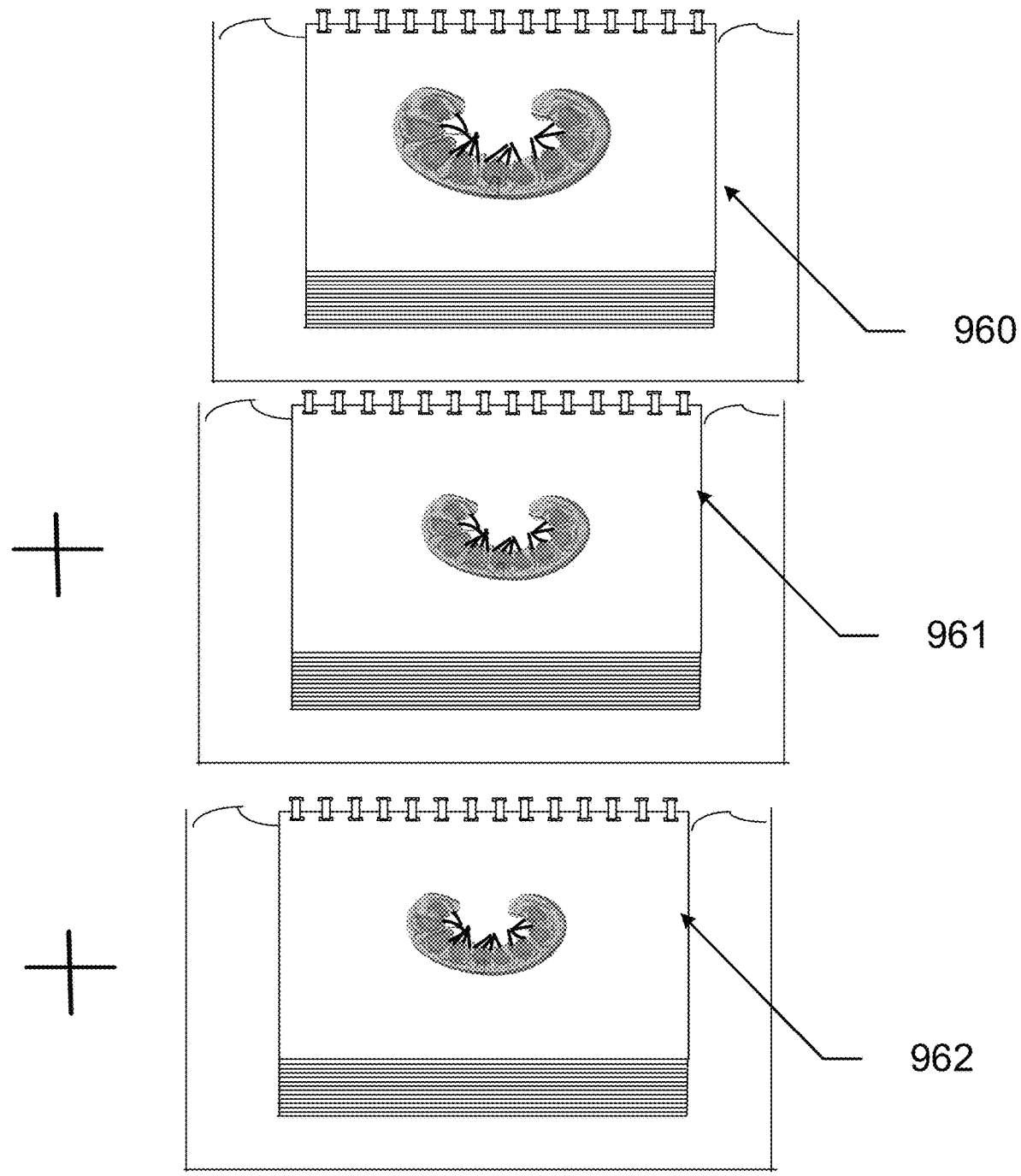
Figure 9D:
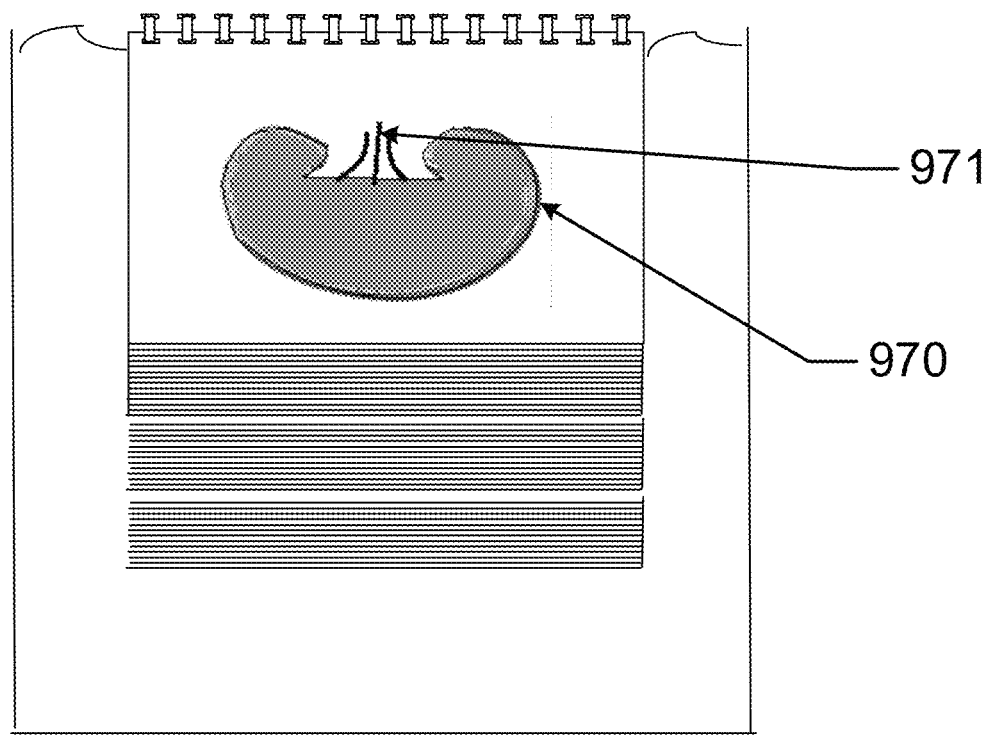

Referring to FIG. 9B, another processing means such as techniques used in microelectronics processing may be used to form matrixes with small form factors. Techniques such as film deposition, resist deposition, reactive ion etching, chemical etching, and other such techniques may be used to form small structures 930. In an example of a kidney production, structure such as the nephron, glomerulus, uretic bud, and the like may have small structure used to create collections of cells that may grow into the small structures 935. Various means may be used to deposit cells of appropriate types upon the small support structures. The support structures may have molecules absorbed to them that attract certain types of cells to bind at appropriate regions. In other examples, layers of cells may be applied or printed in sequential processing to form small structures with differentiated cells in various locations. The sheets of material with the small structures may be applied 940 upon the other printed structures. A number of substrates with small structures 945 may be applied upon the previously printed tissue. In some examples, additional printing steps 950 may be used to print cells that may form vascular structure into appropriate regions of the growing layer which may inter-attach other formed structures 955. Collections of layers processed in the above manners, perhaps dozens or hundreds of such layers may be stacked upon each other and then allowed to grow. Referring to FIG. 9C there layers 960, 961 and 962 may be stacked upon each other. Referring to FIG. 9D, the multiple stacked layers 970 may grow into a formed organ. In some examples additional structures such as the renal veins and arteries 971 as well as ureter structures may be printed into locations between the layers.

Figure 10:
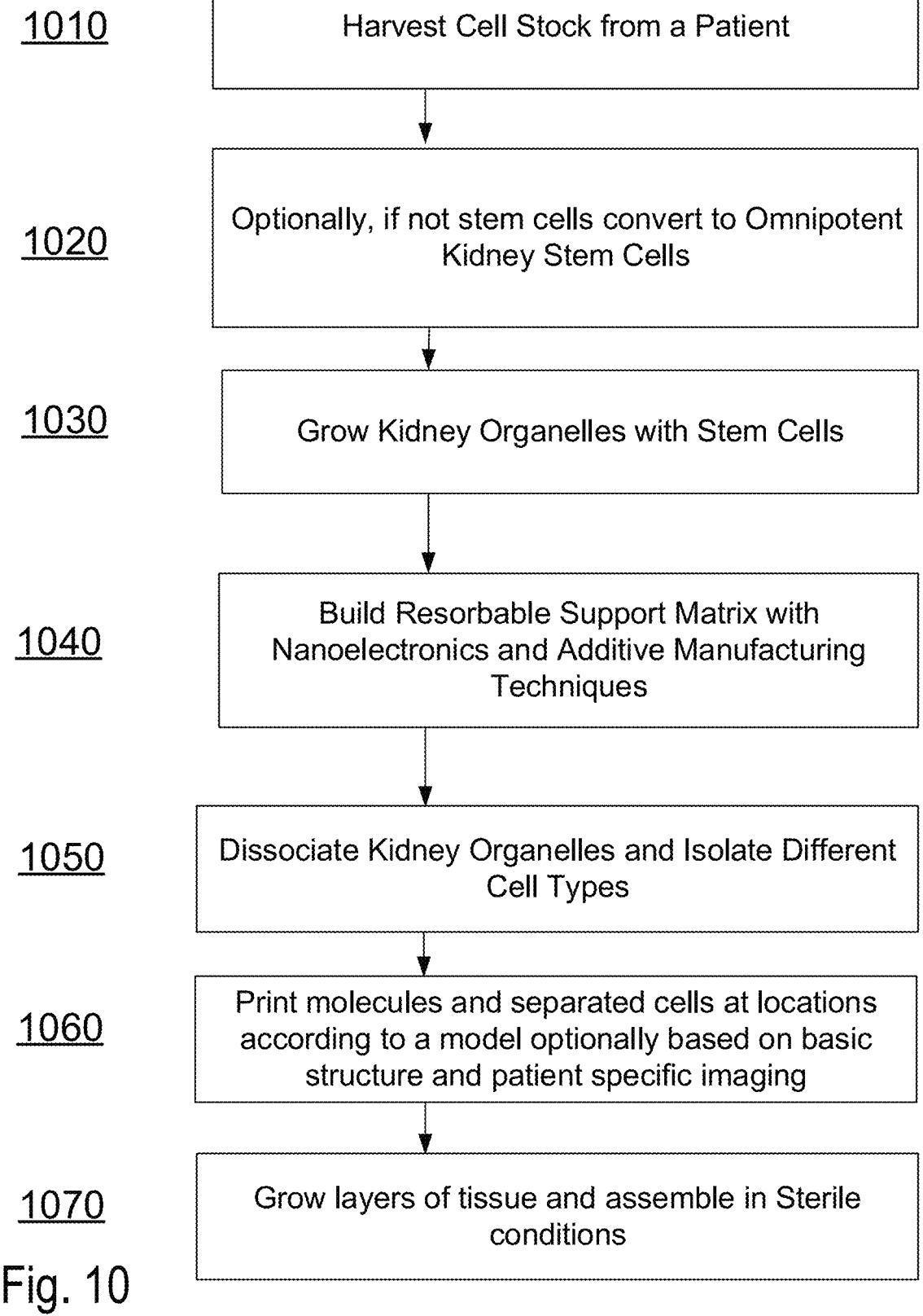
FIG. 10—An exemplary processing flow to produce tissue layers.

Referring to FIG. 10 an exemplary flow is illustrated. At Step 1010 a cell stock may be harvested from a patient. As mentioned earlier, the cell stock may be sorted to isolate existing stem cells from the patient including as a non-limiting example pluripotent stem cells from the Kidney. In other examples, other cells such as fibroblasts may be converted to omnipotent kidney stem cells at step 1020. The isolated or converted cells may be grown at step 1030 to form early stage growth or embryonic type growth of organ related components such as parts of the nephron, uretic body, venous system and the like. In some examples, the growing organ components may be allowed to mature by placing them into a support matrix. In other examples, the early stage organ components may be separated into different cell types which may be further grown up and used to print structures with different cell types. At step 1040, a support matrix may be constructed to support printed cells or otherwise located cells. In some examples, the support matrix may be built to be resorbable into the growing organ tissue, such as from a collagen base for example. The support matrix may be constructed with various techniques include nanoelectronics techniques such as photolithography, reactive ion etching, chemical etching, and film deposition techniques as non-limiting examples. Additive manufacturing techniques may be used to place materials such as molecules of various types upon or into the support matrix. In some example, particular growth factors or other molecules that could support differentiated growth of cell types upon the support matrix may be added with additive manufacturing. In an illustrative example, a rod of support material may be used to lay out the structure of an artery or vein in a tissue layer to be formed. The rod may be printed with cells that surround the rod and grow into a venous form. The rod may include printings of growth factor to encourage or direct the growth of the appropriate differentiated cell type. Nanotechnology may be used to create small controlled structures to form the support matrix.

As mentioned previously, at step 1050, grown structures of cells may be dissociated and then separated to form isolated collections of different cell types which may be fed to printing apparatus. At 1060, the printing apparatus may be used to print both molecules and separated cells at locations according to a model formed to result in a desired organ or tissue layer. The model may be based on basic structural data and may be combined with patient specific imaging data. At step 1070, substrates formed as mentioned above may be placed in sterile locations with correct growth conditions to induce the growth of desired tissue layers. The layers may be assembled in the sterile conditions and allowed to further grow into more mature tissue layers. As the layers mature, fluids such as nutrient containing isotonic fluids may be flowed through the developing organ. The fluids may include blood simulants, or even blood of the patient at stages of the organ or tissue layer growth.

Modelling

There may be many uses for modelling protocols related to the apparatus and methods discussed herein. In some models, imaging data may be used directly to generate models themselves. In other examples, a general model may be supplemented with further resolution from measurements, from theoretical treatments or from artificially generated structural, chemical and cellular models. In an example, an ultra-detailed three-dimensional digital model which may specify the location and type of each individual cell may be created. The method for creating these 3d models may rely on generative design techniques, wherein a unit-element may be defined (a given cell-type) and the overall geometry of a given tissue and/or organ that results may also be defined in a digital model. In some examples, one or more unit elements and the desired tissue construct and a functional/structure "goal" may be used as driving components into a generative design algorithm whose goal is to replicate the overall shape of the tissue and/or organ with details at the level of the specified unit elements. The result may produce a three-dimensional model with structural detail defined with resolution consistent with a cellular level model. This process may be repeated for every tissue and organ in the human body utilizing an appropriate measure or model ensemble of different living cell-types and other structural and/or chemical constructs. Some examples of structural and or chemical constructs may include elements configured of cartilage as a non-limiting example or implanted chemical containing vesicles, which may be self-absorbable, and may contain oxygen or nutrients, energy sources or the like. In some examples, these vesicles may be formed of artificial materials, in other examples they may be formed of naturally occurring materials such as lipids as a non-limiting example. In more complex examples, some models may include a time dependent dimension where the time evolution of a particular printed three-dimensional model when subjected to natural or influenced growth, reorganization or self-organization mechanisms are simulated. Thus, the end functional/structural goal of the model given its time dynamicity, in some examples, may be the result of printing, time evolution, and further steps which influence the growth or deconstruction of regions of the construct.

In some examples, the end/functional or structural goal of the model may be derived from an exemplary Idealized Atlas of the human body. Initial versions of such a goal structure may derive from an imaging-based Atlas of the human body derived and configured on the basis of one or more medical imaging modalities which may include an ensemble of exemplary complete models which can be used as a training dataset. Such imaging may include CT, MR, PET, autopsy, cross sectional cryo-section and ultrasound as non-limiting examples. In some examples, an iterative process, which may be characterized as an artificial intelligence algorithmic process, may start with such an imaging-based Atlas and iterate to one or more models in the Idealized Atlas. Within the iterative process, the resulting machine generated Atlas may be evaluated with human inspection and/or with physical model creation and testing and the like.

An idealized 3d model Atlas may be consistently refined with medical imaging examples with determined outcomes and thus may will be used to further train a machine-learning/AI algorithm.

Once trained, the resultant output of the algorithm may be a digital 3d model, where each voxel may be supplemented with additional dimensions of data such as cell make up, and the like. In some examples, the resulting construct may have the same geometry as the patient's original organ (matching connections, dimensions, etc.), with ultra-fine-detail to the level of individual cell type and placement. In other examples a machine generated model based on the original organ but modified may be the result which may in some examples be reviewed and approved by medical personnel. Any of these resultant digital 3d models may serve as the instructions for the various manufacturing apparatus to produce the engineered tissue or organ.

As discussed additional considerations may be included in the algorithm to determine if improvements to the patient's original anatomy are possible, such as an improved blood flow path and the like. These examples may include the ability to additional locate foreign elements such as electronic, electromechanical, and chemical devices as well as passive type device as have been described heretofore.

As an example, blood flow in a cardiovascular system may be modelled on numerous approaches and principles including in a non-limiting sense Darcy's law, Reynold's number and Poiseuille's equation in regard to the flow characteristics. The location of various tissue types within an organ may be modelled based upon medical imaging techniques. Larger veins, the ureter and the ureter collection system, and basic location of organelles may be modelled based on such imaging. Smaller structures may not be available from standard medical imaging and these may be modeled by various techniques. The cardiovascular system at small scale may include fractal-based modelling with defined boundary conditions based on imaging results. The structure of a nephron may be imaged in destructive techniques which result in a model element that can be replicated in a larger collection that makes up a tissue layer or organ model.

From or with CT/MRI/etc. 3D medical imaging data may be derived from the macro to micro-scale. It may be desirable to image this structural model data with the finest resolution images available in the technology of the imaging apparatus. The resulting data will be used to create a 3D mesh which may be extracted to form the framework of the 3D model. This model may be made patient specific so that it fits seamlessly with the patient's existing anatomy.

In some examples, there may be portions of the anatomy of the tissue layer or the organ which cannot be seen with conventional imaging and thus will be artificially supplied. For example, in a Kidney case these portions may include: glomeruli, bowman's capsule, cortical nephrons, juxtamedullary nephrons, vasa recta, afferent vessels, efferent vessels, intertubular capillaries, interlobular veins, interlobular arteries, spiral tubules, peritubular capillaries, and loops of Henle as non-limiting examples. These structures may be modeled in 3D using traditional 3D modeling techniques and then using specialized and customized shape-packing algorithms, assembled in quantity ranging from 300,000 to 2 million so that the model reflects the number of structures found inside of said patient having been determined through microscopic imaging techniques. Furthermore, the model may be extrapolated and fit within the appropriate geometrical volume and arrangement as would be expected of the natural human anatomy. And still further, the model may include synthesized components that may optimize or otherwise improve a performance metric of the manufactured human organ replacement. In some examples, a tissue engineering and organ manufacturing infrastructure may be used to create non-natural models of structure. That is where, the tissue structures are combined in certain manners that may optimize function or offer new or extended capabilities over natural models.

Modeling techniques may include, but also may not be limited to the following: creating the path in three dimensions using a series of curves; sweeping circular cross sections corresponding to the correct diameter of the given anatomical structure along the created curve-paths; cutting curve path from a solid block using inverse/cutting sweep function along created curves corresponding to the correct diameter of the given anatomical structure; using a pipe-creating function to create hollow tubular structure along curves; and/or in three dimensions creating a series of circles corresponding to the overall location/path and diameter of a given anatomical structure and lofting through those circles.

The modelling techniques may also include making said circles solid double-walled, i.e. a circle within a circle and lofting the hollow pipe structure in a single pass; making outer structure and removing inner structure through Boolean subtraction; making inner surface and thickening to create tubular structure; overlaying an image or illustration of a nephron, scaling it to the appropriate real-world size digitally, and tracing it, followed by employing techniques above. In some examples, a 3D model will then be processed to a format acceptable for directing photolithography manufacturing systems to manufacture said model Materials There may be various materials that are of use in the concepts herein. The materials that make up a resorbable support may include, for example, resorbable collagen or synthetic materials. Layers of films may be added together for different function. For example, a double layer of a collagen film may allow for the formation of channels in the void there between. Techniques to join the layers to form the extrema of the channels may include application of adhesives or directed growth of cellular layers that close off the peripheries. There may be numerous growth factors and other biomolecules that may be important to direct differentiation, spur or support growth and the like.

Micropipette Arrays and Microfluidic Processors

Figure 11A:
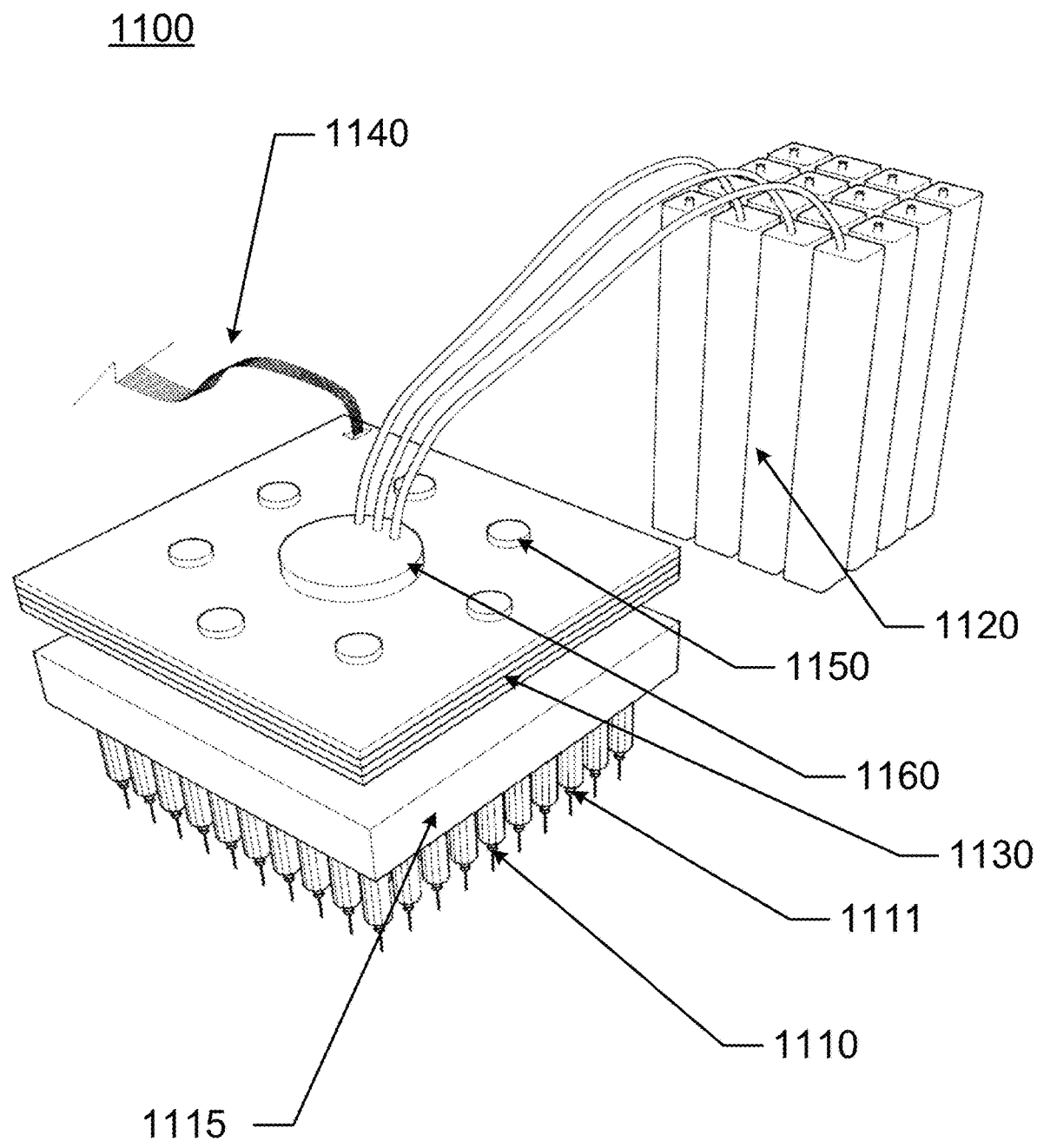
FIGS. 11A-B—An exemplary printing system to produce tissue layers and organs.

Referring to FIG. 11A, an exemplary tissue engineering printing device is presented. In some examples, a printing head 1100 may include a multitude of syringe type printing nozzles (1110,1111 for examples) which dispense a calibrated amount of material in response to a control signal which may be conveyed by numerous power and signal transmission circuits 1140. Syringe elements may include customized or standard pipetting components which are made of materials consistent with the handling of biological and cellular materials. In some examples, the dispensing array 1115 may be connected with a supply source 1120 of the material that it is printing. In some examples, a vessel 1160 containing a liquid suspension of the biologic material may be placed in physical connection with the micropipette array 1115.

In other examples, a microfluidic processor 1130 may process cellular and biological material and interface which each of the pipetting devices independently. Thus, a collection of cells may be grown and nourished with electroactive control of a microfluidic processor. Thereafter, the collection of cells may be separated by the action of the microfluidic processor. As a non-limiting example of how this could function, a collection of cells may be dosed by microfluidic means with a series of dyes that are sensitive to surface proteins of differentiated cell types or to genetic sequences being expressed in other examples. A photo-absorption based portion of the microfluidic array may sort individualized cells based on the type of dyes that are presented with the cell as it progresses in a microfluidic channel. In other examples, various sorting techniques as may be known in the art may be employed instead.

The microfluidic channel may activate one particular path in response to absorption of a particular wavelength related to a particular type of cell. The cell may then be shunted to a reservoir 1150 containing cells of the particular type. Thereafter, that reservoir may be uniquely connected to one or more of the multitude of dispensing elements. Other reservoirs may be connected to other elements in some examples. Thus, the micropipette array may be used to dispense particular cell types at controlled locations in space.

In other examples, other media such as growth media, solutions containing particular chemical and protein based signaling aspects and other materials may be collected in a reservoir associated with certain micropipette components of the array. In some examples, the reservoirs of the cells may be further processed to create collections of cells that may be surrounded in a protective membrane that keeps the cells in a particular environmental state while the printing process occurs. In some examples, for example, the protective membrane surrounding the cells may adhere to portions of a support structure that has been printed to locate cells in a given three-dimensional state. As a cell collection binds to a location, the outer coating may dissolve or otherwise dissipate and allow printed cells to being interacting with each other and carry on various collective processes such as "self" assembling into organelle structures, or differentiating into various structures.

The micropipette arrays may include nozzles configured for single cell distribution as well as distribution of collections. And the arrays may include a multitude of the nozzles in various patterns for efficient printing. In some examples, a print head may include tens to hundreds of individual elements. In some examples there may be thousands of nozzles configured in a print head. In some examples there may be tens of thousands or more nozzles configured in a print head.

As printing occurs a substrate supporting various aspects such as support structures, collections of cells and fluid may be built in three-dimensional space. In some examples, the substrate may be lowered a single level at a time after the modelled cells locations for a level have been printed. In some examples, a single level may correspond to the thickness of a single cell, in other examples the movement may correspond to a dimension related to a collection of cells. Additional aspects of the processing of the cell printing device may include the use of improved motors (servo or otherwise), sterile containers to maintain the living cells for deposition, local temperature and environmental controls specific to the local area of the substrate, pipettes, tubing, and any other areas which living cells pass through. In addition, there may be configuration and design aspects of the control algorithms which control the movements of the heads and rate of living cell deposition, and motor controls. In some examples the pipets may include the ability to move independently of the collection in one or more directions. In some examples, the entire print head may be capable of a gimble type movement of an angle of pivot around an axis.

In some examples the micropipette arrays may include needle type points that may be moved in space by the motors which drive the collection of elements of the array. In some of these examples, the printing may be carried out into a gel type substrate where a semisolid type relationship is conveyed by the gel being injected into. In some examples, the gel may contain important growth and sustenance aspects such as chemical, protein, and dissolved oxygen for example. In some examples, blood vessels may be formed in initial steps of printing a three-dimensional tissue or organ construct. The blood vessels may be utilized to provide the growth and sustenance aspects as well. In some examples, an artificial blood stimulant may be used to provide oxygen, energy related chemicals and the like and to remove wastes including gasses. In other examples, the gel substrate may be formed with channels that carry out the function of vessels until they form in the tissue construct itself.

Figure 11B:
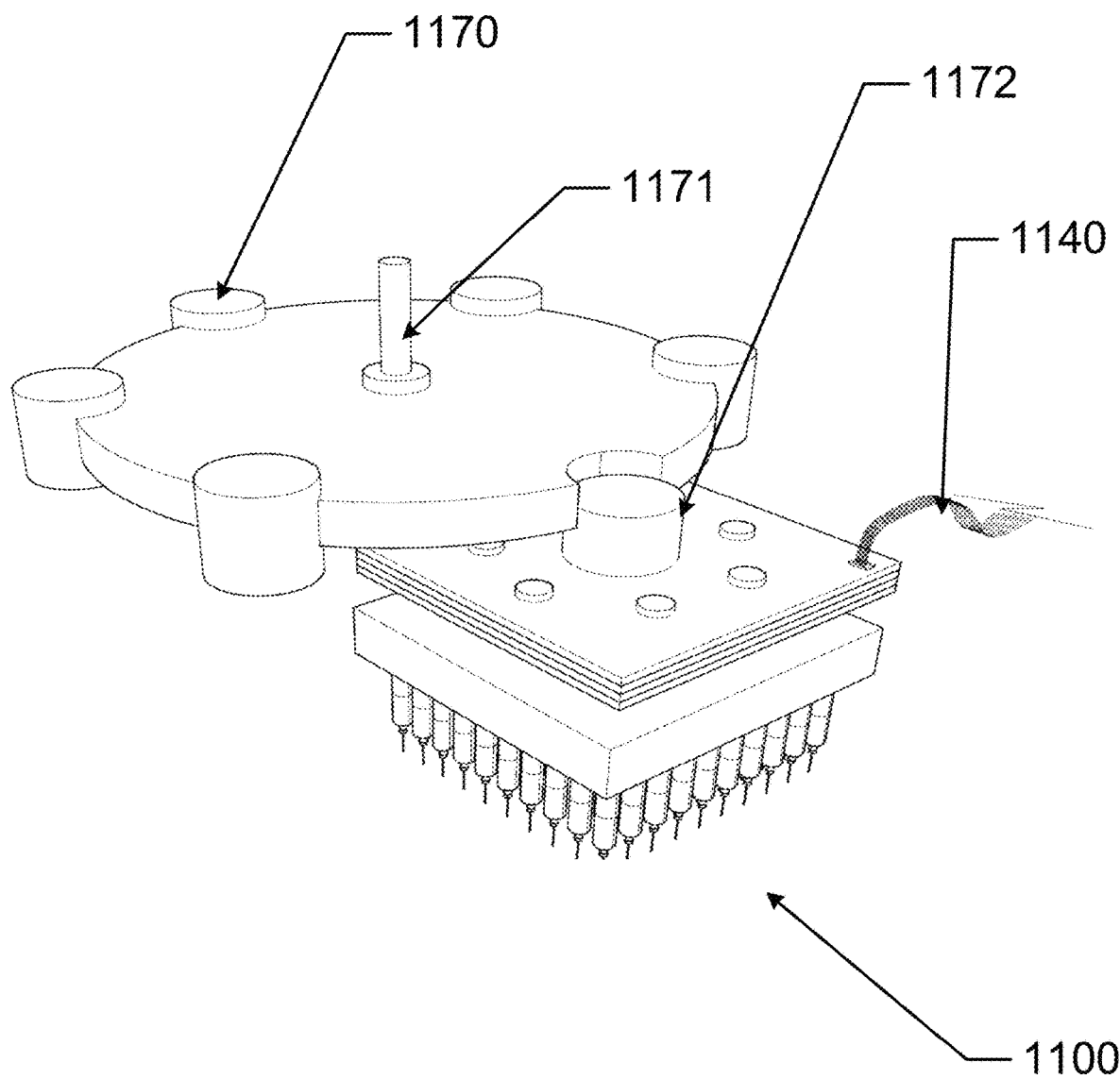

Referring to FIG. 11B, a different type of example of sample distribution is illustrated. A multi-pipette array distribution device 1100 may be supplied with vessels 1170 containing materials to print. The vessels may be supplied to the printing device from external supplies. In the example, an inventory of vessels may be contained on a stocking device that may rotate around an axis 1171 moving a desired source of materials 1172 into position to interface with the printing apparatus 1100. There may be numerous manners to supply materials to an additive manufacturing print head to create organ and tissue structures according to the methods herein.

In some examples a microgravity environment, or a simulated microgravity environment/neutral buoyancy environment may be used for the environment of the printing process while it is used for the printing.

Exemplary Tissue Engineering System Overview

Figure 12C:
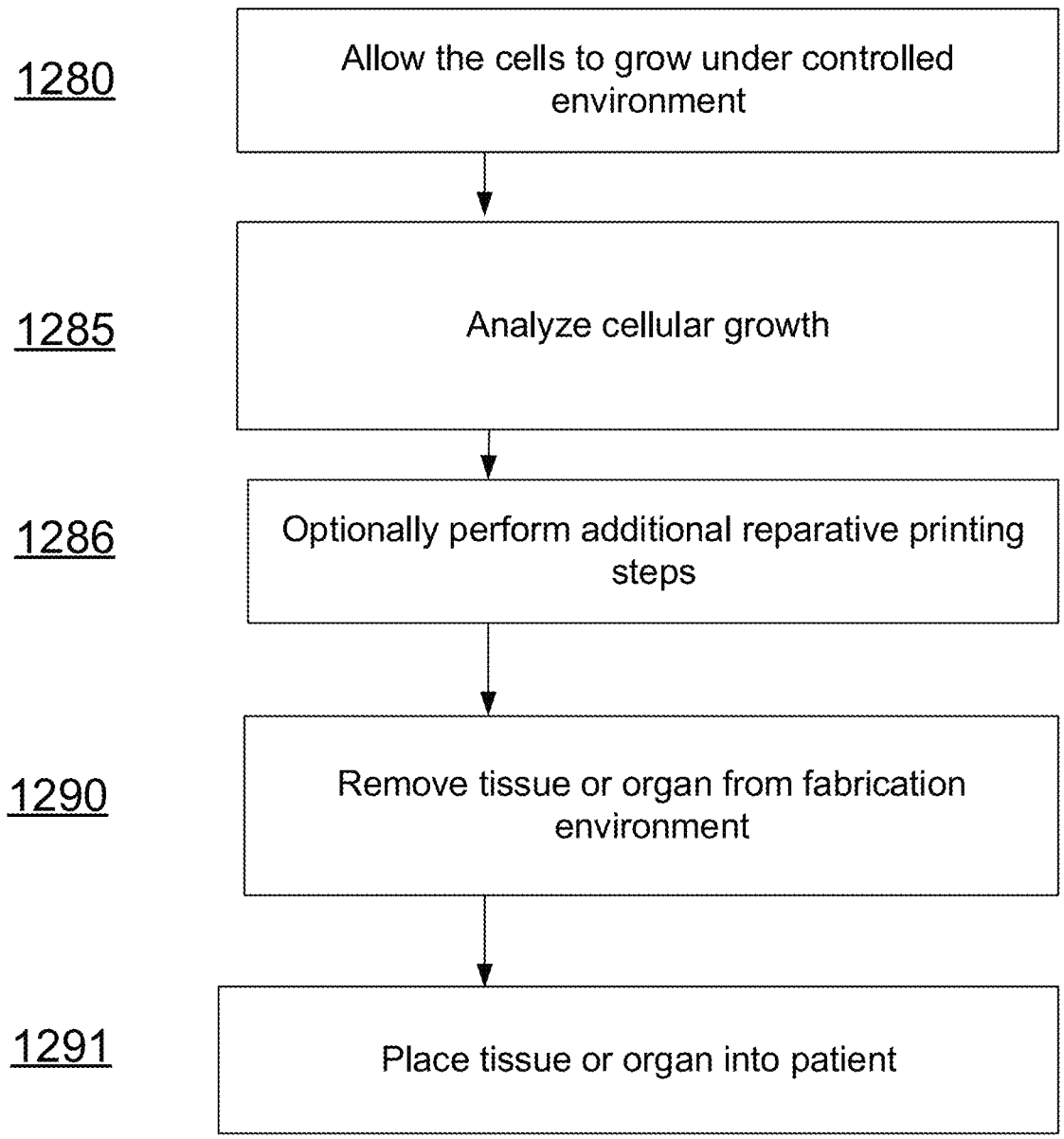

Referring to FIGS. 12A-12C an exemplary processing flow for tissue engineering production is found. At step 1210 a collection of processing tools is assembled into a manufacturing line. In preferred examples, the manufacturing line is configured in a cleanspace fabricator as has been described herein. A collection including in a non-limiting sense, printing devices, incubation/growth environments, cell production equipment, cell genetic modification equipment and the like are configured into the production line and sterilized. In preferred environments, the equipment set may have single use components for the portions which touch or interact with the cellular matter of a particular tissue engineering production run. After a tissue or organ is produced, if the result is the last for the particular patient, the single use components would be replaced out. In the case of a cleanspace fabricator, the equipment may be changed out from the peripheral location of each of the processing tools.

At step 1220, measurements may be performed on a particular patient. In some examples, an imaging study may be used to perform at least some of the measurements. In a non-limiting example an MRI imaging study may be used to extract a physical model of a patient's heart, it may include the three-dimensional structure of the organ, where its major and minor blood vessels are located, where valves are located, amongst other information. Other measurements may relate to health metrics in non-physical manners such as electrocardiograms, blood tests, and the like which may also be collected and/or aggregated from previous tests on the individual.

The patient's genome may be studied for the patient at step 1225. The genome may contain information related to genetic influenced defectivity of functional aspects of the organ or tissue in question. An artificial intelligence program may be used to correlate models to the patient's genomic data in reference to abundant medical data of patients with similar symptomology and genetic sequencing. In other examples, other means of analyzing the genetic data may be employed to understand genetic mutations that may be correlated to medically relevant defectiveness or reduced efficacy of the operation of cells in tissues or organs.

In some examples, at step 1230 samples of cells may be obtained from the patient. In some examples, the tissue or organ of the patient may be biopsied to extract omnipotent or pluripotent stem cells. In other examples, general cells such as epithelial cells may be sampled from the patient. The cells may be subjected to genetic modification at step 1235. For example, a CRISPR based genetic editing protocol, as has been described herein, may be performed to edit genome sequences that may be deemed undesirable. In some examples, the modifications to render the cells pluripotent as discussed previously may be performed. In some examples, modifications to the cells may be performed to impart overt identifying characteristics to the cells such as a photo-absorption or luminescent aspect in non-limiting examples. The cells may be treated in manners to cause them to grow, and a population of the cells may be formed at step 1240.

While the previous steps are being performed, or even before they are performed, an analysis may be performed on the result of the patient measurements and on databases related to tissue structure and function at steps 1245. In some examples, the analysis may be supported by artificial intelligence algorithmic operation. The result of the analysis may create a physical model of the tissue or organ, at least to a resolution of the imaging data 1250. For structural dimensions smaller than the resolution of imaging, a model may be created at step 1251. In some examples, the artificial intelligence algorithm may be capable of inferring a structure of sub-resolution sized features. In some other examples, generic models of small structure may be applied as an overlay to the larger scale structure. In still further examples, cells of the appropriate type may be printed into a general region and then allowed to self-assemble into the sub-dimensional appropriate structure as it forms naturally. In some examples the artificial intelligence algorithm may complete an analysis on the measurement data and calculate a probability of an improved structure/function with a different model of cell locations and types. Such calculated modifications may be reviewed by medical professionals for concurrence or acceptance of the model modifications.

In some examples, the cells sampled from the patient may be immediately placed within the fabricator environment. In other examples, the cells may be modified in an external facility and delivered to the fabricator environment. In either event, before the cells are placed within the fabricator environment, the environment may be subjected to a sterilization protocol at step 1255.

Cells may be delivered to the sterilized environment and may be processed in equipment within the fabrication environment at step 1260. Within the processing environment and dependent on the details of the model a tissue engineering process may be initiated. In some examples, a model-based scaffold may be created at step 1265. In some examples, a gel scaffold may be produced based on the model. At step 1270, different cell types may be printed, in some cases upon or within the scaffold, based on model direction. In some examples, at step 1275, nutritive layers may be imprinted upon the printed cell types. In other examples, the printing of nutritive layers may precede the printing of the cells. In some examples, either during the processing of a scaffold layer or during or after the printing of different cell types devices of various types may be placed or affixed to the scaffold or growing tissue layers for either temporary or permanent inclusions. In some of these examples, passive or active electronic, electromechanical, electrosensing, passive chemical releasing devices and electrically active chemical releasing devices may be placed or imprinted as non-limiting examples. In some examples, both the scaffolding and any added passive or active electronic or non-electronic devices may be resorbable or dissolvable over time.

Cells may be allowed to grow at step 1280. In some examples, nutrition and other resources needed by cells may be provided continuously into the matrix of growing cells. These resources may be provided through liquid that the growing cells are immersed within. In other examples, a gel matrix may include the equivalent of vessels to provide nutrition while a vascular system of the tissue or organ develops. The vascular system may be utilized to provide nutrition and other resource distribution as soon as it is able to function. In some examples a vascular system may be grown before other portions of the tissue are printed, and then a subsequent printing process may create another portion of the tissue or organ.

In some examples, at step 1285 the growing tissue or organ may be analyzed by measurement protocols within the fabrication environment. In some examples thermal sensors may provide a three-dimensional map of metabolism in the tissue. In other examples imaging techniques such as labeled glucose PET, or the equivalent of a functional MRI study may be employed. The measurement protocols may show regions of the growing tissue that are not growing appropriately. In such cases, additional printing steps of chemical/biochemical treatments to the appropriate region may occur 1286, or the supplementation of cellular material may be printed into the matrix.

In some examples, at step 1290, the tissue may be removed from the fabrication environment and placed into a patient with a surgical procedure 1291.

Organ Systems

In the examples provided herein, a large focus has been given to examples related to Kidney and Heart cells, tissues, and organs. These examples are only illustrative for the many types of tissue and organs that may be created using the principals disclosed herein. For example, skin tissues, cartilage, bone, lymphatic, and vascular tissues may be formed in similar manners using the techniques and apparatus disclosed herein. Furthermore, many organ systems may similarly be processed or tissue layers of them may be processed including but not limited to heart, liver, pancreas, lung, spleen, stomach, intestine, brain, esophagus, thyroid, gall bladder and tongue as non-limiting examples. As well, these tissues and organs may be produced and used in various types of organisms including but not limited to humans. Body elements that may comprise various tissue types such as ears, eyes, nose, skin with hair, and the like may also be processed in the type of apparatus described here. Therefore, the examples are not meant to limit to just one tissue or organ type.

Glossary of Selected Terms

Reference may have been made to different aspects of some preferred embodiments of the invention, examples of which are illustrated in the accompanying drawings. A Glossary of Selected Terms is included now at the end of this Detailed Description.

Air receiving wall: a boundary wall of a cleanspace that receives air flow from the cleanspace.

Air source wall: a boundary wall of a cleanspace that is a source of clean airflow into the cleanspace.

Annular: The space defined by the bounding of an area between two closed shapes one of which is internal to the other.

Automation: The techniques and equipment used to achieve automatic operation, control or transportation.

Ballroom: A large open cleanroom space devoid in large part of support beams and walls wherein tools, equipment, operators and production materials reside.

Batches: A collection of multiple substrates to be handled or processed together as an entity Boundaries: A border or limit between two distinct spaces—in most cases herein as between two regions with different air particulate cleanliness levels.

Circular: A shape that is or nearly approximates a circle.

Clean: A state of being free from dirt, stain, or impurities—in most cases herein referring to the state of low airborne levels of particulate matter and gaseous forms of contamination.

Cleanspace (or equivalently Clean Space): A volume of air, separated by boundaries from ambient air spaces, that is clean.

Cleanspace, Primary: A cleanspace whose function, perhaps among other functions, is the transport of jobs between tools.

Cleanspace, Secondary: A cleanspace in which jobs are not transported but which exists for other functions, for example as where tool bodies may be located.

Cleanroom: A cleanspace where the boundaries are formed into the typical aspects of a room, with walls, a ceiling and a floor.

Conductive Connection: a joining of two entities which are capable of conducting electrical current with the resulting characteristics of metallic or semiconductive or relatively low resistivity materials.

Conductive Contact: a location on an electrical device or package having the function of providing a Conductive Surface to which a Conductive Connection may be made with another device, wire or electrically conductive entity.

Conductive Surface: a surface region capable of forming a conductive connection through which electrical current flow may occur consistent with the nature of a conductive connection.

Core: A segmented region of a standard cleanroom that is maintained at a different clean level. A typical use of a core is for locating the processing tools.

Ducting: Enclosed passages or channels for conveying a substance, especially a liquid or gas—typically herein for the conveyance of air.

Envelope: An enclosing structure typically forming an outer boundary of a cleanspace.

Fab (or fabricator): An entity made up of tools, facilities and a cleanspace that is used to process substrates.

Fit up: The process of installing into a new clean room the processing tools and automation it is designed to contain.

Flange: A protruding rim, edge, rib, or collar, used to strengthen an object, hold it in place, or attach it to another object. Typically, as utilized herein, a Flange may also be used to seal the region around the attachment.

Folding: A process of adding or changing curvature.

HEPA: An acronym standing for high-efficiency particulate air. Used to define the type of filtration systems used to clean air.

Horizontal: A direction that is, or is close to being, perpendicular to the direction of gravitational force.

Job: A collection of substrates or a single substrate that is identified as a processing unit in a fab. This unit being relevant to transportation from one processing tool to another.

Logistics: A name for the general steps involved in transporting a job from one processing step to the next. Logistics can also encompass defining the correct tooling to perform a processing step and the scheduling of a processing step.

Maintenance Process: A series of steps that constitute the repair or retrofit of a tool or a toolPod. The steps may include aspects of disassembly, assembly, calibration, component replacement or repair, component inter-alignment, or other such actions which restore, improve or insure the continued operation of a tool or a toolPod Multifaced: A shape having multiple faces or edges.

Nonsegmented Space: A space enclosed within a continuous external boundary, where any point on the external boundary can be connected by a straight line to any other point on the external boundary and such connecting line would not need to cross the external boundary defining the space.

Perforated: Having holes or penetrations through a surface region. Herein, said penetrations allowing air to flow through the surface.

Peripheral: Of, or relating to, a periphery.

Periphery: With respect to a cleanspace, refers to a location that is on or near a boundary wall of such cleanspace. A tool located at the periphery of a primary cleanspace can have its body at any one of the following three positions relative to a boundary wall of the primary cleanspace: (i) all of the body can be located on the side of the boundary wall that is outside the primary cleanspace, (ii) the tool body can intersect the boundary wall or (iii) all of the tool body can be located on the side of the boundary wall that is inside the primary cleanspace. For all three of these positions, the tool's port is inside the primary cleanspace. For positions (i) or (iii), the tool body is adjacent to, or near, the boundary wall, with nearness being a term relative to the overall dimensions of the primary cleanspace.

Planar: Having a shape approximating the characteristics of a plane.

Plane: A surface containing all the straight lines that connect any two points on it.

Polygonal: Having the shape of a closed figure bounded by three or more line segments Process: A series of operations performed in the making or treatment of a product—herein primarily on the performing of said operations on substrates.

Processing Chamber (or Chamber or Process Chamber): a region of a tool where a substrate resides or is contained within when it is receiving a process step or a portion of a process step that acts upon the substrate. Other parts of a tool may perform support, logistic or control functions to or on a processing chamber.

Process Flow: The order and nature of combination of multiple process steps that occur from one tool to at least a second tool. There may be consolidations that occur in the definition of the process steps that still constitute a process flow as for example in a single tool performing its operation on a substrate there may be numerous steps that occur on the substrate. In some cases, these numerous steps may be called process steps in other cases the combination of all the steps in a single tool that occur in one single ordered flow may be considered a single process. In the second case, a flow that moves from a process in a first tool to a process in a second tool may be a two-step process flow.

Production unit: An element of a process that is acted on by processing tools to produce products. In some cleanspace fabricators this may include carriers and/or substrates.

Robot: A machine or device that operates automatically or by remote control, whose function is typically to perform the operations that move a job between tools, or that handle substrates within a tool.

Round: Any closed shape of continuous curvature.

Substrates: A body or base layer, forming a product, that supports itself and the result of processes performed on it.

Tool: A manufacturing entity designed to perform a processing step or multiple different processing steps. A tool can have the capability of interfacing with automation for handling jobs of substrates. A tool can also have single or multiple integrated chambers or processing regions. A tool can interface to facilities support as necessary and can incorporate the necessary systems for controlling its processes.

Tool Body: That portion of a tool other than the portion forming its port.

Tool Chassis (or Chassis): An entity of equipment whose prime function is to mate, connect and/or interact with a toolPod. The interaction may include the supply of various utilities to the toolPod, the communication of various types of signals, the provision of power sources. In some embodiments a Tool Chassis may support, mate or interact with an intermediate piece of equipment such as a pumping system which may then mate, support, connect or interact with a toolPod. A prime function of a Tool Chassis may be to support easy removal and replacement of toolPods and/or intermediate equipment with toolPods.

toolPod (or tool Pod or Tool Pod or similar variants): A form of a tool wherein the tool exists within a container that may be easily handled. The toolPod may have both a Tool Body and also an attached Tool Port and the Tool Port may be attached outside the container or be contiguous to the tool container. The container may contain a small clean space region for the tool body and internal components of a tool Port. The toolPod may contain the necessary infrastructure to mate, connect and interact with a Tool Chassis. The toolPod may be easily transported for reversible removal from interaction with a primary clean space environment.

Tool Port: That portion of a tool forming a point of exit or entry for jobs to be processed by the tool. Thus, the port provides an interface to any job-handling automation of the tool.

Tubular: Having a shape that can be described as any closed figure projected along its perpendicular and hollowed out to some extent.

Unidirectional: Describing a flow which tends to proceed generally along a particular direction albeit not exclusively in a straight path. In clean airflow, the unidirectional characteristic is important to ensuring particulate matter is moved out of the cleanspace.

Unobstructed removability: refers to geometric properties, of fabs constructed in accordance with the present invention that provide for a relatively unobstructed path by which a tool can be removed or installed.

Utilities: A broad term covering the entities created or used to support fabrication environments or their tooling, but not the processing tooling or processing space itself. This includes electricity, gasses, airflows, chemicals (and other bulk materials) and environmental controls (e.g., temperature).

Vertical: A direction that is, or is close to being, parallel to the direction of gravitational force.

Vertically Deployed Cleanspace: a cleanspace whose major dimensions of span may fit into a plane or a bended plane whose normal has a component in a horizontal direction. A Vertically Deployed Cleanspace may have a cleanspace airflow with a major component in a horizontal direction. A Ballroom Cleanroom would typically not have the characteristics of a vertically deployed cleanspace.

While the invention has been described in conjunction with specific embodiments, it is evident that many alternatives, modifications and variations will be apparent to those skilled in the art in light of the foregoing description. Accordingly, this description is intended to embrace all such alternatives, modifications and variations as fall within its spirit and scope.

What is claimed is:

1. A method of forming a tissue layer comprising:
configuring a tissue engineering apparatus comprising:
a cleanspace fabricator, wherein the cleanspace fabricator is configured to process at least a first substrate comprising tissue layers, wherein the cleanspace fabricator maintains both a particulate cleanliness as well as a biological sterility cleanliness, wherein the cleanspace fabricator comprises at least a first processing apparatus and a second processing apparatus deployed along a periphery of the cleanspace fabricator, and wherein the cleanspace fabricator comprises automation to move one or more of the first substrate and the first processing apparatus within a primary cleanspace of the cleanspace fabricator;
a modelling system, wherein the modelling system is configured to produce a first digital model which is used to control at least the first processing apparatus, wherein the first processing apparatus controls equipment to create one or more of a tissue support matrix and a printed deposit of cellular and molecular material;
wherein the first processing apparatus comprises a second substrate with a multitude of printing elements arrayed thereupon, wherein the multitude of printing elements are capable of emitting a fluid comprising at least a first cell to a region within the first processing apparatus based upon a final three-dimensional model; and
wherein the first processing apparatus further comprises a microfluidic processing system to process cellular and chemical material and deliver a product to the multitude of printing elements;
placing a first substrate within the cleanspace fabricator;
performing a medical imaging technique upon a patient;
creating the first digital model, wherein an input to the first digital model includes at least the results of the medical imaging technique;
refining the first digital model to create a final digital model, wherein the final digital model represents a three-dimensional model for depositing of cellular material and wherein the refining is performed by an algorithmic processing of the first digital model;
forming two or more individual printing system elements;
aligning the two or more individual printing system elements in space relative to the first substrate;
obtaining a tissue sample from the patient;
processing the tissue sample within the microfluidic processing system to create a first stock of cells, wherein the microfluidic processing system isolates cells of different cell types, and wherein the microfluidic processing system performs a genetic modification protocol on at least a cell from the tissue sample;
printing a tissue support matrix comprised of a gelled material, wherein the gelled material comprises channels within its form through which fluids may flow, and wherein the gelled material is one or both of absorbable by a growing tissue in contact with the gelled material or dissolvable with fluids of the growing tissue or fluids flowed through the tissue support matrix; and
printing cells from the first stock of cells into the gelled tissue support matrix using an array of micropipettes, wherein each of the micropipettes comprise sharp needles to penetrate the gelled material and to reach locations in three dimensionally accessible regions of the gelled tissue support matrix, and wherein the array of micropipettes uses location control signals that are based upon the final digital model.

2. A tissue engineering apparatus comprising:
a cleanspace fabricator, wherein the cleanspace fabricator is configured to process at least a first substrate comprising tissue layers, wherein the cleanspace fabricator maintains both a particulate cleanliness as well as a biological sterility cleanliness, wherein the cleanspace fabricator comprises at least a first processing apparatus and a second processing apparatus deployed along a periphery of the cleanspace fabricator, and wherein the cleanspace fabricator comprises automation to move one or more of the first substrate and the first processing apparatus within a primary cleanspace of the cleanspace fabricator;
a modelling system, wherein the modelling system is configured to produce a first three dimensional model which is used to control at least the first processing apparatus, wherein the first processing apparatus controls equipment to create one or more of a tissue support matrix and a printed deposit of cellular and molecular material, and wherein the modelling system comprises a first processor to perform algorithmic processes of machine learning upon an atlas of imaging data from one or more imaging modalities, and wherein the first processor further performs a generative design algorithm to synthesize one or more of at least a first unit element, a desired tissue construct and a structural goal into the first three dimensional model as a composite of a result of the machine learning processing of the atlas of imaging data and a result of the generative design algorithm;
wherein the first processing apparatus comprises a second substrate with a multitude of printing elements arrayed thereupon, wherein the multitude of printing elements are capable of emitting a fluid comprising at least a first cell to a region within the first processing apparatus based upon a final three-dimensional model; and
wherein the first processing apparatus further comprises a microfluidic processing system to process cellular and chemical material and deliver a product to the multitude of printing elements.

3. The tissue engineering apparatus of claim 2 wherein the final three-dimensional model is the same as the first three-dimensional model.

4. The tissue engineering apparatus of claim 2 further comprising:
wherein the final three-dimensional model is derived from the first three-dimensional model; and
wherein an artificial intelligence algorithm adjusts the first three-dimensional model to create a new model that the artificial intelligence algorithm evaluates as more effective as measured across a set of evaluation metrics assessed by the artificial intelligence algorithm.

5. The tissue engineering apparatus of claim 2 wherein the printing elements are arranged into an array, and wherein the printing elements comprise individual micropipettes.

6. The tissue engineering apparatus of claim 5 wherein the first processing apparatus creates a tissue support matrix comprised of a gelled material.

7. The tissue engineering apparatus of claim 6 wherein the gelled material creates an approximately neutral buoyancy environment for the printed deposit.

8. The tissue engineering apparatus of claim 6 wherein the gelled material comprises channels within its form through which fluids may flow.

9. The tissue engineering apparatus of claim 8 wherein the gelled material is one or both of absorbable by a growing tissue in contact with the gelled material or dissolvable with fluids of the growing tissue or fluids flowed through the growing tissue.

10. The tissue engineering apparatus of claim 6 wherein a micropipette array comprises sharp needles through which the printing deposit flows and wherein the sharp needles penetrate the gelled material to reach locations in three dimensionally accessible regions of the gelled tissue support matrix.

11. The tissue engineering apparatus of claim 10 wherein individual micropipettes of the micropipette array are fastened to actuators that allow a degree of independent movement from the array as a whole.

12. The tissue engineering apparatus of claim 10 wherein the tissue engineering apparatus is capable of functioning in a micro-gravity environment.

13. A method of forming a tissue layer comprising:
configuring a tissue engineering apparatus comprising:
a cleanspace fabricator, wherein the cleanspace fabricator is configured to process at least a first substrate comprising tissue layers, wherein the cleanspace fabricator maintains both a particulate cleanliness as well as a biological sterility cleanliness, wherein the cleanspace fabricator comprises at least a first processing apparatus and a second processing apparatus deployed along a periphery of the cleanspace fabricator, and wherein the cleanspace fabricator comprises automation to move one or more of the first substrate and the first processing apparatus within a primary cleanspace of the cleanspace fabricator;
a modelling system, wherein the modelling system is configured to produce a first digital model which is used to control at least the first processing apparatus, wherein the first processing apparatus controls equipment to create one or more of a tissue support matrix and a printed deposit of cellular and molecular material;
wherein the first processing apparatus comprises a second substrate with a multitude of printing elements arrayed thereupon, wherein the printing elements are capable of emitting a fluid comprising at least a first cell to a region within the first processing apparatus based upon a final three-dimensional model; and
wherein the first processing apparatus further comprises a microfluidic processing system to process cellular and chemical material and deliver a product to the printing elements;
placing a first substrate within the cleanspace fabricator;
performing a medical imaging technique upon a patient;
creating the first digital model, wherein an input to the first digital model includes at least the results of the medical imaging technique;
refining the first digital model to create a final digital model, wherein the final digital model represents a three-dimensional model for depositing of cellular material and wherein the refining is performed by an algorithmic processing of the first digital model;
forming two or more individual printing system elements;
aligning the two or more individual printing system elements in space relative to the first substrate;
obtaining a tissue sample from the patient;
isolating a first sample of at least a first cell type from the tissue sample;
growing a first stock of cells from the first sample; and printing cells from the stock of cells upon the first substrate, using location control signals that are based upon the final digital model.

14. The method of claim 13 further comprising:
genetically modifying cells of the isolated first sample, wherein the genetic modification renders the cell to be an omnipotent stem cell;
growing organelles using the omnipotent stem cell;
dissociating the organelles; and
sorting the cells from the organelles into different cell types.

15. The method of claim 13 further comprising genetically modifying cells of the isolated first sample, wherein the genetic modification alters a genetic mutation of a cell from the tissue sample from the patient.

16. The method of claim 15 wherein the genetic modification includes a CRISPR-Cas9 protocol.

17. The method of claim 13 wherein the refining of the first digital model comprises:
performing algorithmic processes of machine learning upon an atlas of imaging data from one or more imaging modalities; and
wherein the modelling system further performs a generative design algorithm to synthesize one or more of at least a first unit element, a desired tissue construct and a structural goal to create the final digital model as a composite of a result of the machine learning processing of the atlas of imaging data and a result of the generative design algorithm and the first digital model.

18. The method of claim 13 wherein the first stock of cells is processed within the microfluidic processing system.

19. The method of claim 18 wherein the microfluidic processing system isolates cells of different cell types.

20. The method of claim 19 wherein the microfluidic processing system performs a genetic modification protocol on at least a cell from the first stock of cells.

* * * * *